United States Patent
Deans et al.

(10) Patent No.: US 9,851,307 B2
(45) Date of Patent: Dec. 26, 2017

(54) DEVICE AND METHODS FOR DETECTION OF ANALYTES INCLUDING USE OF A COLORIMETRIC BARCODE

(71) Applicant: FLIR Detection, Inc., Stillwater, OK (US)

(72) Inventors: Robert Deans, Grafton, MA (US); Peter G. Loges, Natick, MA (US); William McDaniel, Shrewsbury, MA (US); Kateri E. Paul, Medford, MA (US); Lawrence F. Hancock, North Andover, MA (US); Matthew Joseph Szabo, Stillwater, OK (US)

(73) Assignee: FLIR Detection, Inc., Stillwater, OK (US)

( * ) Notice: Subject to any disclaimer, the term of this patent is extended or adjusted under 35 U.S.C. 154(b) by 151 days.

(21) Appl. No.: 14/651,500

(22) PCT Filed: Dec. 18, 2013

(86) PCT No.: PCT/US2013/076072
§ 371 (c)(1),
(2) Date: Jun. 11, 2015

(87) PCT Pub. No.: WO2014/100150
PCT Pub. Date: Jun. 26, 2014

(65) Prior Publication Data
US 2015/0316483 A1 Nov. 5, 2015

Related U.S. Application Data

(60) Provisional application No. 61/740,009, filed on Dec. 20, 2012.

(51) Int. Cl.
*G01N 21/76* (2006.01)
*G01N 21/78* (2006.01)
(Continued)

(52) U.S. Cl.
CPC ............ *G01N 21/76* (2013.01); *B01L 3/5023* (2013.01); *G01N 21/78* (2013.01); *G01N 31/22* (2013.01);
(Continued)

(58) Field of Classification Search
CPC ..... B01L 2300/0627; B01L 2300/0681; B01L 2300/0861; B01L 2300/087;
(Continued)

(56) References Cited

U.S. PATENT DOCUMENTS

| 5,109,691 A | 5/1992 | Corrigan et al. |
| 5,296,380 A | 3/1994 | Margalit |

(Continued)

FOREIGN PATENT DOCUMENTS

WO    WO 97/37212 A1    10/1997

OTHER PUBLICATIONS

International Search Report and Written Opinion for PCT/US2013/076072 dated Apr. 18, 2014.
(Continued)

*Primary Examiner* — Maureen Wallenhorst
(74) *Attorney, Agent, or Firm* — Haynes and Boone, LLP

(57) ABSTRACT

Embodiments described herein related to devices and methods for the collection and/or determination of analytes, such as illicit substances including military explosives, explosives, and precursors thereof. In some cases, the device may be a disposable device that incorporates highly efficient sample collection in combination with microfluidic-based chemical analysis resulting in the rapid detection and identification of unknown materials. In some cases, multiple colorimetric detection chemistries may be employed, and the resulting "barcode" of color changes can be used to positively identify the presence and/or identity of the analyte.

24 Claims, 18 Drawing Sheets

(51) Int. Cl.
*G01N 31/22* (2006.01)
*B01L 3/00* (2006.01)
*G01N 21/66* (2006.01)
*G01N 21/77* (2006.01)

(52) U.S. Cl.
CPC ............... *B01L 2300/0627* (2013.01); *B01L 2300/0681* (2013.01); *B01L 2300/087* (2013.01); *B01L 2300/0861* (2013.01); *B01L 2300/12* (2013.01); *G01N 21/66* (2013.01); *G01N 2021/7786* (2013.01); *G01N 2201/10* (2013.01); *Y10T 436/2575* (2015.01)

(58) Field of Classification Search
CPC ............... B01L 2300/12; B01L 3/5023; G01N 2021/7786; G01N 21/66; G01N 21/76; G01N 21/78; G01N 21/84; G01N 2201/10; G01N 31/22; G01N 33/22; Y10T 436/17; Y10T 436/173076; Y10T 436/19; Y10T 436/206664; Y10T 436/25; Y10T 436/255; Y10T 436/2575
USPC ......... 436/79, 106, 110, 124, 135, 164, 165, 436/172, 174, 178, 180; 422/400, 401, 422/402, 408, 411, 412, 413, 414, 418, 422/419, 425, 430, 82.05, 82.08, 82.09, 422/502, 503, 507; 506/12, 39
See application file for complete search history.

(56) References Cited

U.S. PATENT DOCUMENTS

| | | | |
|---|---|---|---|
| 5,455,606 | A | 10/1995 | Keeling |
| 5,648,047 | A | 7/1997 | Kardish et al. |
| 5,929,422 | A | 7/1999 | Lappe |
| 7,368,292 | B2 | 5/2008 | Hummel et al. |
| 7,605,367 | B2 | 10/2009 | Miller et al. |
| 7,666,684 | B2 | 2/2010 | Swager et al. |
| 8,597,590 | B2 * | 12/2013 | Yue .................. B01L 3/502707 422/402 |
| 2004/0132218 | A1 * | 7/2004 | Ho ........................ B01L 3/5025 436/524 |
| 2005/0101027 | A1 | 5/2005 | Haas |
| 2006/0204401 | A1 | 9/2006 | Woudenberg et al. |
| 2007/0202009 | A1 * | 8/2007 | Nunes .................. B01L 3/5023 422/400 |
| 2008/0190220 | A1 * | 8/2008 | Backes ................ B29C 66/542 73/864.81 |
| 2009/0221085 | A1 | 9/2009 | Pagoria et al. |
| 2010/0129922 | A1 | 5/2010 | Gold et al. |
| 2011/0045517 | A1 | 2/2011 | Derringer et al. |
| 2012/0178176 | A1 | 7/2012 | Haas et al. |
| 2012/0301371 | A1 * | 11/2012 | Augstein ............... B01F 1/0027 422/502 |
| 2014/0080129 | A1 | 3/2014 | Klunder et al. |

OTHER PUBLICATIONS

International Preliminary Report on Patentability for PCT/US2013/076072 dated Jul. 2, 2015.
Adams et al., Demonstration of Submersible High-Throughput Microfluidic Immunosensors for Underwater Explosives Detection. Anal. Chem. 2011. 83: 8411-9. dx.doi.org/10.1021/ac2009788.
Bell et al., A Microfluidic Device for Presumptive Testing of Controlled Substances. J Forensic Sci, Jul. 2007. 52(4): 884-8. doi: 10.1111/j.1556-4029.2007.00478.x.
Pumera, Analysis of explosives via microchip electrophoresis and conventional capillary electrophoresis: A Review. Electrophoresis. Jan. 1, 2006. 27(1): 244-56. E Publication Nov. 5, 2005. DOI: 10.1002/elps.200500609.
Sarazin et al., Capillary and Microchip Electrophoretic Analyses of Explosives and their Residues. Separation & Purification Reviews. 2010. 39:63-94. DOI: 10.1080/15422119.2010.529226.
Settles, Fluid Mechanics and Homeland Security. Annual Rev. Fluid Mech. 2006. 38:87-110.
Sieben et al., Microfluidic colourimetric chemical analysis system: Application to nitrate detection. Anal. Methods. The Royal Society of Chemistry. Feb. 19, 2010. 2:484-91. DOI: 10.1039/c002672g.
Verpoorte, Microfluidic chips for clinical and forensic analysis. Electrophoresis 2002. 23: 677-712.

* cited by examiner

① Sample

② Crush vial and shake to mix

③ Insert into cassette

④ Read results

*Manually*

*or with a smart phone application*

(a) Meisenheimer Complex Formation (b) Griess Reaction (c) [Pt(typ)Cl]PF$_6$ Perchlorate Test (d) Hydrolytic Boronate Deprotection (e)

Nitrate Ester &
Nitramine Detection
(multi-step reaction)

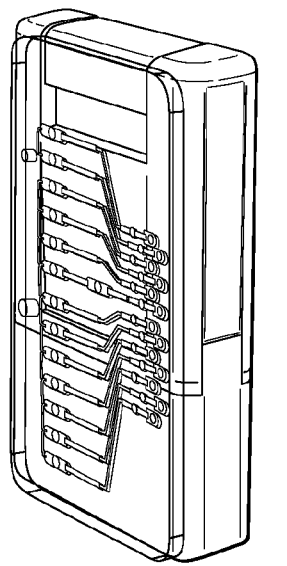
1. Open package
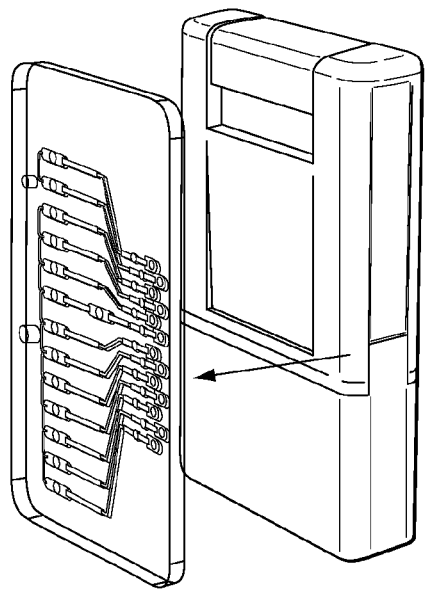
2. Separate analysis cassette from sample collection device
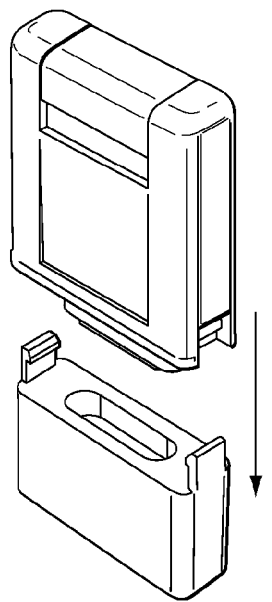
3. Remove cap for sample collection
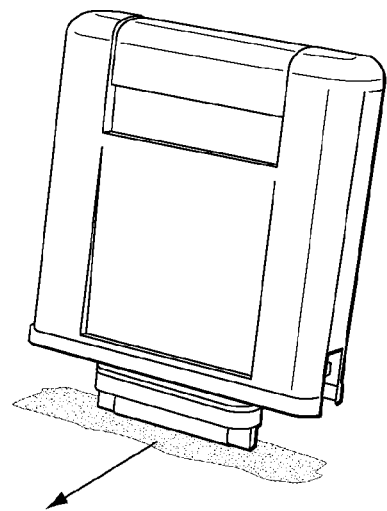
4. Roll across surface to collect sample
Fig. 10-1

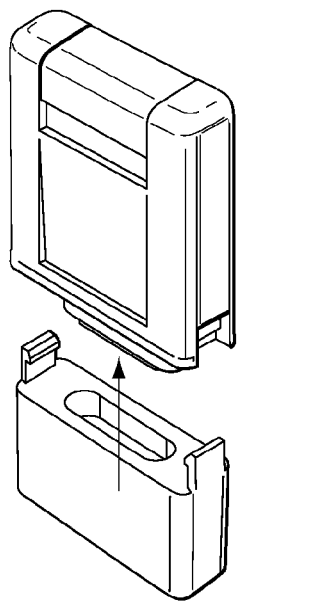
5. Replace cap
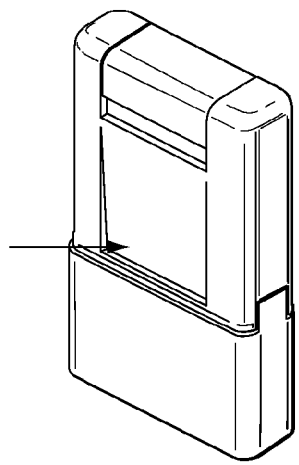
6. Depress solvent release
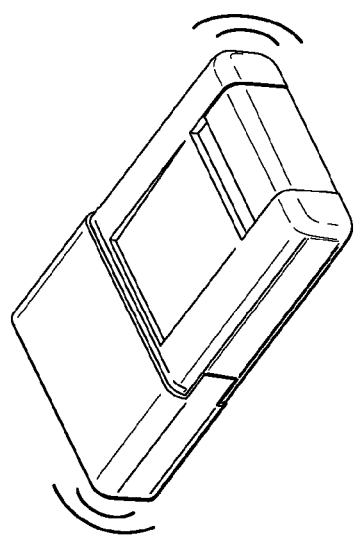
7. Shake
Fig. 10-2

8. Snap into analysis cassette

9. Depress plunger to release sample

10. Wait for chemistries to develop and read results (i) three-dimensional view (ii) two-dimensional view (i) without analysis cover (ii) with analysis cover

DEVICE AND METHODS FOR DETECTION OF ANALYTES INCLUDING USE OF A COLORIMETRIC BARCODE

RELATED APPLICATIONS

This application is a national stage filing under 35 U.S.C. §371 of International Application No. PCT/US2013/076072, filed Dec. 18, 2013, which claims priority under 35 U.S.C. §119(e) to U.S. Provisional Application No. 61/740,009, filed Dec. 20, 2012. The contents of each of these applications are incorporated herein by reference in their entireties for all purposes.

STATEMENT REGARDING FEDERALLY SPONSORED RESEARCH OR DEVELOPMENT

This invention was made in part with Government support under N41756-11-C-3876 awarded by the Navy Engineering Logistics Office. The Government has certain rights in the invention.

FIELD OF THE INVENTION

Embodiments described herein generally relate to devices and methods for the collection and/or determination of analytes including chemical and biological warfare agents, drugs, toxic industrial chemicals and metals, gunshot residue, military and homemade explosives, other controlled substances, and precursors thereof.

BACKGROUND OF THE INVENTION

The rapid detection and identification of homemade explosives is vitally important in military, homeland security, humanitarian, and environmental applications. Colorimetric approaches are valuable due to their relatively low cost, excellent sensitivity, fast speed, portability, and simple operational requirements (e.g., no additional power, equipment or training necessary, enabling rapid deployment in remote areas). While commercially available aerosol- or liquid-based colorimetric kits for explosives detection exist, many expose the user to toxic reagents and/or are prone to false positives.

SUMMARY OF THE INVENTION

The present invention relates to various devices, kits, and methods for determining an analyte.

In some embodiments, the method comprises providing a sample analysis device comprising at least 5 channels constructed and arranged to receive a sample suspected of containing an analyte, each channel comprising a different chemical reagent; and simultaneously introducing the sample into the at least 5 channels such that the analyte, if present, interacts with one or more of the chemical reagents to produce a determinable signal.

In some embodiments, the method comprises providing a sample analysis device comprising a plurality of channels constructed and arranged to receive a sample suspected of containing an analyte, each channel comprising a different chemical reagent, each chemical reagent capable of generating a luminescent or colorimetric signal; and simultaneously introducing the sample into the plurality of channels such that the analyte, if present, interacts with one or more of the chemical reagents to produce a plurality of luminescent or colorimetric signals, thereby determining the analyte, wherein the presence and/or identity of the analyte is determined without need for a non-luminescent or non-colorimetric analysis of the sample.

In some embodiments, the method comprises providing a sample collection device comprising a rolling substrate, the rolling substrate having a surface; contacting the surface of the rolling substrate with an article suspected of containing an analyte via a rolling or tapping motion such that a sample suspected of containing the analyte is collected on the surface of the rolling substrate; contacting the surface of the rolling substrate with a fluid carrier to transfer at least a portion of the sample to the fluid carrier to produce a fluid sample suspected of containing the analyte; introducing the fluid sample suspected of containing the analyte into a sample analysis device comprising a plurality of channels constructed and arranged to receive the fluid sample, wherein portions of the fluid sample are simultaneously introduced into each of a set of the plurality of channels, each of the set of channels comprising a different chemical reagent capable of generating a luminescent and/or colorimetric signal upon interaction with a specific analyte, wherein the analyte, if present in the fluid sample, interacts with one or more of the chemical reagents to produce a plurality of luminescent and/or colorimetric signals in at least some of the set of channels; and determining the presence and/or identity of the analyte based on the plurality of luminescent and/or colorimetric signals.

Devices for determining analytes are also provided. In some embodiments, the device comprises a sample collection portion arranged on a first region of the device and comprising a sample collection well; a sample collection substrate detachably attached to the device and capable of being inserted into the sample collection well; and a sample analysis portion arranged on a second region of the device and in fluid communication with the sample collection portion, the sample analysis portion comprising: at least one fluid container containing a fluid carrier, at least one channel comprising a chemical reagent capable of generating a luminescent or colorimetric signal, and a mixing chamber in fluid communication with the at least one fluid container, the at least one channel, and the sample collection substrate, wherein the sample collection portion and the sample analysis portion are integrally connected to one another.

In some embodiments, sample analysis devices for determining an analyte are provided. In some embodiments, the sample analysis device comprises a sample inlet constructed and arranged to receive a sample suspected of containing an analyte; and at least 5 channels in fluid communication with the sample inlet and constructed and arranged for essentially simultaneous analysis of an analyte suspected of being present in a sample introduced into the inlet, each channel comprising a different chemical reagent in substantially solid form, wherein the analyte, if present, interacts with one or more of the chemical reagents to produce a determinable signal.

In some embodiments, the sample analysis device comprises a sample inlet constructed and arranged to receive a sample suspected of containing an analyte; and a plurality of channels in fluid communication with the sample inlet, each channel comprising a different chemical reagent, each chemical reagent capable of generating a luminescent or colorimetric signal, wherein the analyte, if present, interacts with one or more of the chemical reagents to produce a plurality of luminescent or colorimetric signals, wherein the device does not include a crystallizing reagent.

In some embodiments, kits for determining an analyte are provided. In some embodiments, the kit comprises a sample collection device, comprising: a first region comprising a fluid container containing a fluid carrier; a second region comprising a surface constructed and arranged to contact an article suspected of containing the analyte and to receive fluid from the fluid container; a sample outlet in fluid communication with the first and second regions; and a housing containing the first region, the second region, and the sample outlet; and a sample analysis device, comprising: at least one sample inlet constructed and arranged to receive a sample suspected of containing an analyte from the sample outlet of the sample collection luminescent device; and a channel in fluid communication with the sample inlet, the channel comprising a chemical reagent capable of generating a luminescent or colorimetric signal.

BRIEF DESCRIPTION OF THE DRAWINGS

FIGS. 10-1, 10-2, and 10-3 show schematic representations of the various steps for analyte detection using a method described herein.

Figure 1:
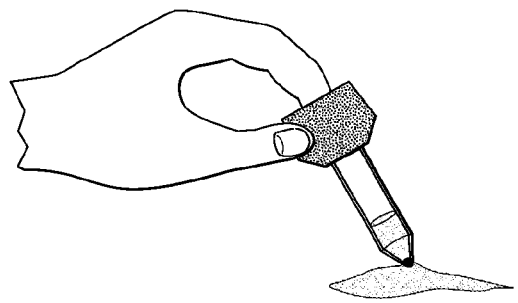
FIG. 1 shows a method for determination of an analyte, according to one embodiment.
Figure 1:
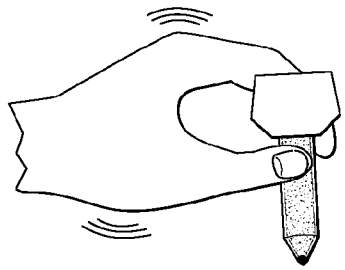
Figure 1:
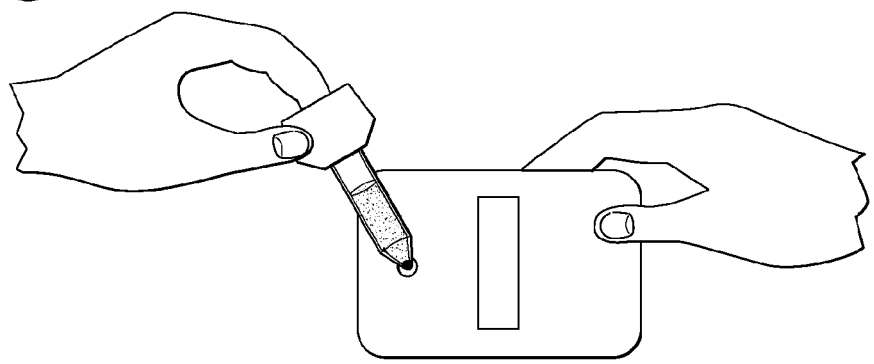
Figure 1:
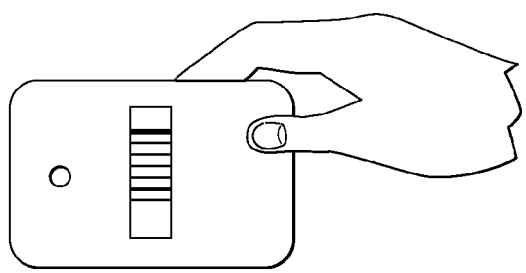
Figure 1:
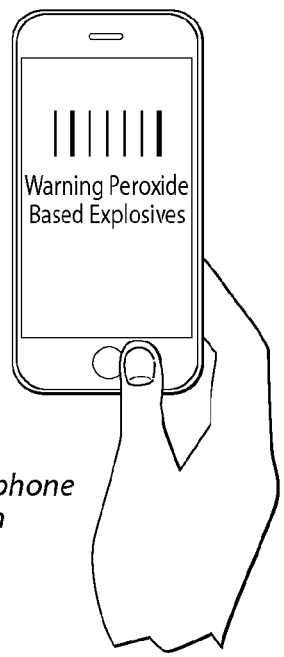

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein related to devices, kits, and methods for the collection and/or determination of analytes, such as illicit substances including military explosives, homemade explosives, drugs, chemical and biological warfare agents, toxic industrial chemicals and metals, gunshot residue, other controlled substances, and precursors thereof. In some cases, the devices, kits, and methods described herein may be useful in the detection of improvised explosive devices (IEDs) incorporating homemade explosive components, as well as in homeland security operations. Such devices may provide enhanced homemade explosive precursor detection capabilities in a user-friendly format with lower false positive rates. In some cases, the devices are disposable. In some embodiments, multiple colorimetric detection chemistries may be performed (e.g., simultaneously) and the resulting array of color changes (e.g., "barcode" of color changes) can be used to positively identify the presence and/or identity of the analyte.

Some embodiments described herein provide kits, devices, and methods that combine highly efficient sample collection with microfluidic-based chemical analysis, resulting in the rapid detection and identification of unknown materials. For example, a kit may include a sample collection device and a sample analysis device. In some embodiments, the sample collection device and the sample analysis device may be provided as two physically separate components that may be detachably attached to one another at various steps during operation. Two objects are "detachably attached" when one object is attached to another object in such a manner that the object s may be physically separated and, if needed, physically re-attached, by an operator without requiring disassembly of the individual objects and/or without the need for the use of any tools. In some embodiments, the sample collection device and the sample analysis device may be provided in an assembled form, but may be physically separated into two distinct components during operation. In some cases, the sample collection device and the sample analysis device may be detachably attached and/or physically separated at various points during operation of the device to determine an analyte. In another set of embodiments, a sample collection portion and a sample analysis portion may be integrally attached within a single device. Typically, a sample suspected of containing an analyte is collected using the sample collection device or portion and then delivered to the sample analysis device or portion for determination of the analyte(s).

FIG. 1 shows an illustrative embodiment where (1) a sample is contacted with a surface of a sample collection device; (2) an internal fluid reservoir within the sample collection device is crushed to release a fluid carrier and the sample collection device is shaken to combine the fluid carrier with the sample; (3) the sample collection device may then be connected to a sample analysis device, releasing the sample and fluid carrier into the sample analysis device. Capillary action may wick the sample and fluid carrier into a reaction zone of the sample analysis device (e.g., pre-loaded with various detection chemistries), and (4) the resultant array of color changes indicating positive or negative results may be observed within a relatively short timeframe (e.g., ~1 minute) to determine any analyte present.

In one set of embodiments, the device includes a sample collection device or sample collection portion that may be used to contact the surface of an article suspected of being associated with (e.g., containing) a target analyte to collect a sample. The analyte may be determined, in some cases, by direct sampling of the analyte or by sample of an article suspected of containing the analyte. For example, the analyte may be concealed in a container, and a surface of the container may be sampled by the sample collection device or sample collection portion. In some embodiments, a surface of the analyte or article may be physically contacted or swiped by the sample collection device or sample collection portion. The sample may be in a substantially solid form (e.g., in particulate form), or may be in the form of a liquid, such as a solution, suspension, dispersion, or other mixture. In some cases, the sample may be a vapor-phase sample. The collected sample may then be combined with a fluid carrier and may be analyzed as described herein.

The sample collection device or sample collection portion may include one or more sample collection substrates. In some cases, the sample collection device or sample collection portion may include a plurality of sample collection substrates for collecting multiple samples. For example, multiple samples may be collected in the event that the analysis conditions (e.g., solvents) for one test are incompatible with the analysis conditions for another test. The multiple samples collected may be analyzed simultaneously or sequentially as desired. In some cases, the sample collection device or sample collection portion may include a first sample collection substrate, where sample is collected and then processed for analysis, and, optionally, a second sample collection substrate, where sample may be stored for subsequent confirmatory testing. The sample collection substrate(s) may be arranged in combination with a sample collection well on the device such that, in operation, the sample collection substrate(s) may be combined with a fluid carrier (e.g., solvent) within the sample collection well. In some embodiments, the sample collection well may be arranged on another component (e.g., a sample lid) that may be detachably attached to the device such that, when attached to the device, the component and device may form an enclosed region within which sample collection substrate(s) may be combined with a fluid carrier.

In some embodiments, the sample collection substrate may be detachably attached to the device. For example, the sample collection substrate may be provided attached to the device (e.g., attached to the sample collection portion of the device). In operation, the sample collection substrate may be detached from the device by the user and contacted with a sample suspected of containing an analyte (e.g., a solid sample, liquid sample, vapor sample, etc.) and then re-attached to the device for sample analysis. In some embodiments, the sample collection substrate containing the sample may be re-attached to the device such that the sample collection substrate is positioned within the sample collection well. Fluid carrier from another region of the device may be delivered to the sample collection well, for example, to dissolve or otherwise mix with the collected sample on the sample collection substrate.

In some cases, the sample collection substrate includes a substantially planar surface that may be contacted with an article suspected of containing an analyte, for example, via a swiping motion. As an illustrative embodiment, the sample collection substrate portion may include a substantially planar substrate such as a borosilicate material. It may be desirable in some cases to arrange the substrate in combination with a filter material, such as a gas-permeable filter (e.g., polytetrafluoroethylene or PTFE). Those of ordinary skill in the art would be capable of selecting a substantially planar sample collection substrate having the appropriate material, size, surface morphology, and the like, to suit a particular application. For example, the substantially planar sample collection substrate may be selected to include a material that does not adversely react with the sample, solvents, or other reagents of the device while also retaining the ability to capture and release the sample, solvents or other reagents. Examples of materials that may be useful as sample collection substrates include borosilicate materials, filter paper, open-cell foams, Nomex®, Teflon®, various cloths (e.g., muslin), adhesive-coated substrates, and the like.

In some cases, the sample collection substrate includes a substantially non-planar surface. For example, the sample collection substrate may include a rolling substrate, the surface of which may be contacted with an article suspected of containing an analyte via a rolling, tapping, or other motion. Such rolling substrates may increase the efficiency of sample collection. In some embodiments, the rolling substrate is a substantially cylindrical substrate. In some embodiments, the rolling substrate is a substantially spherical substrate.

The rolling substrate may be selected to exhibit certain chemical and mechanical properties that may enhance sample collection efficiency, as well as manufacturability of the device. In some cases, the rolling substrate may comprise a hydrophilic material. For example, the hydrophilic material may include ionized and/or hydrogen-bonding moieties. In some cases, the rolling substrate may comprise a hydrophobic material such as polytetrafluoroethylene (PTFE). In some cases, the rolling substrate may be selected to exhibit a particular mechanical strength. For example, a relatively soft, tacky material (e.g., Post-It® note adhesive) may be suitable for harvesting particulate matter while a hard, dry material (e.g., texturized with micropores or macroscale grooves) may be more amenable to larger volume sample introduction.

In some cases, the rolling substrate may be functionalized with a material that enhances sample collection efficiency. For example, the rolling substrate may be coated or functionalized with an adhesive material (e.g., a repositionable adhesive material). Examples of adhesive materials include pressure sensitive adhesive or tape. Those of ordinary skill in the art would be capable of selecting the appropriate adhesive material for use within the context of embodiments described herein.

Those of ordinary skill in the art would be capable of selecting a rolling substrate having the appropriate material, size, surface morphology, and the like, to suit a particular application. For example, the rolling substrate may be selected to meter a substantially uniform dose of analyte sample into a sample analysis device or sample analysis portion, allowing for determination of analytes ranging from trace surface contamination to bulk samples and eliminating any detrimental effects of over-sampling or under-sampling.

Figure 5:
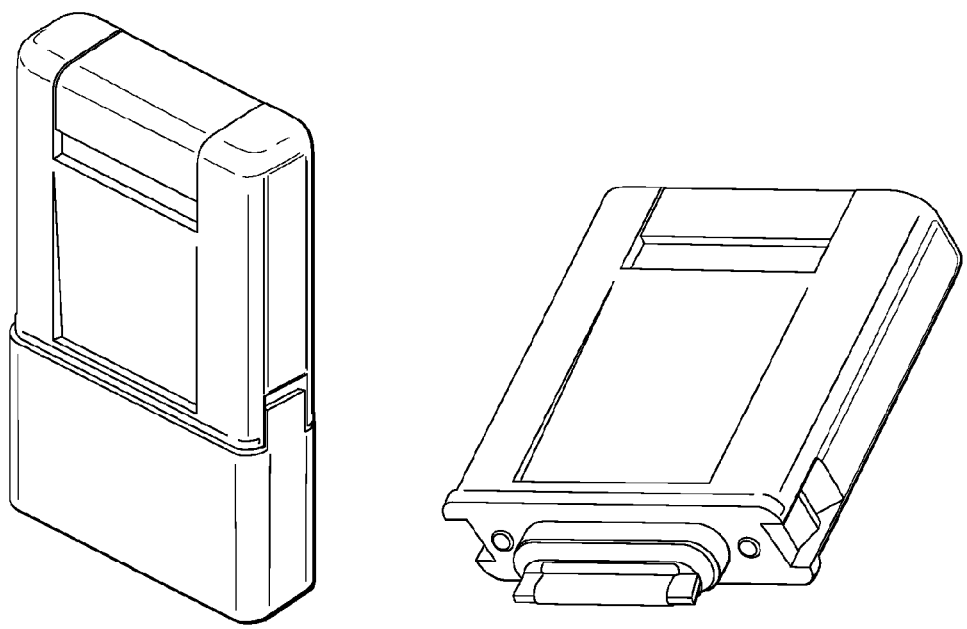
FIG. 5 shows mock-ups, as well as a schematic representation, of a sampler subcomponent of a device as described herein.
Figure 5:
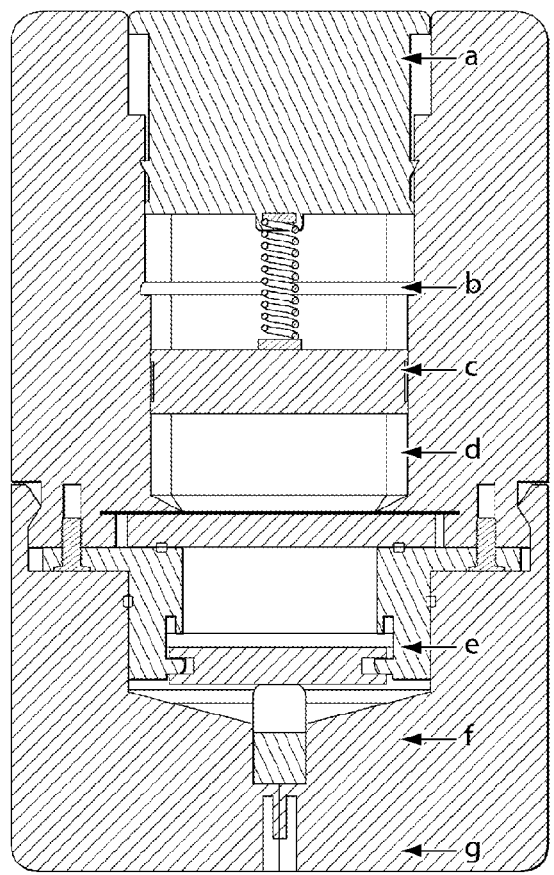

In some embodiments, the sample collection device or sample collection portion may include additional compartments and/or components that facilitate efficient collection and release of a sample. For example, the sample collection device or sample collection portion may incorporate an internal solvent-filled chamber to aid in the release of the sample. The sample collection device or sample collection portion may be constructed and arranged such that, upon contact of the substrate with an article suspected of containing the analyte, the substrate may be contacted with a fluid carrier released from an internal fluid container to produce a liquid sample containing the analyte. The internal fluid container may be designed to dispense a fluid carrier to the sample collection substrate, for example, upon disruption of a seal, upon application of mechanical force by a plunger, and/or the like. The sample collection device or sample collection portion may further include a sample outlet for release of the liquid sample, for example, into a sample analysis device or sample collection portion, and optionally a housing. FIG. 5 shows schematic representations of an exemplary sample collector device including (a) a plunger actuator, (b) plunger lock grooves, (c) plunger, (d) fluid reservoir, (e) rolling substrate, (f) particle/air filter, and (g) analysis cassette connection. FIG. 12 shows another embodiment of such internal solvent-filled chambers or "blister buttons."

To optimize release efficiency of the analyte from the sample collection substrate, the fluid carrier may be selected to exhibit excellent solubility for a particular analyte. Other considerations include the pressure to be applied by the sample collection substrate for efficient analyte collection, the surface area to be sampled, and the time required to completely dissolve the sample on the sample collection substrate in the fluid carrier. Simple screening tests may be used to evaluate the suitability of a fluid carrier for a particular application. For example, a surface, contaminated with a known mixture of analytes (e.g., explosives) can be prepared and contacted with a sample collection substrate. Extraction and analysis of the components captured by the sample collection substrate may be performed, in addition to quantifying the material dissolved by fluid carrier.

Devices described herein may also include a sample analysis device or sample analysis portion for evaluating the sample collected by the sample collection device or sample collection portion. The sample analysis device or sample analysis portion may include at least one sample inlet (e.g., one sample inlet, two sample inlets) constructed and arranged to receive a sample from the sample collection device or sample collection portion (e.g., a sample outlet of the sample collection device). In some cases, the sample analysis device or sample analysis portion may include a microfluidic-based platform for analyzing the sample. In some embodiments, the sample analysis device or sample analysis portion includes a channel in fluid communication with the sample inlet, within which a chemical reagent capable of generating a luminescent or colorimetric signal is positioned. In some cases, the sample analysis device or sample analysis portion includes at least 5, at least 10, at least 15, at least 20, at least 55, or more, channels in fluid communication with the sample inlet.

In some cases, the sample analysis device or sample analysis portion includes a mixing chamber positioned between, and in fluid communication with, the sample collection substrate(s) and the channel(s), where the collected sample may be dissolved in or mixed with solvents from one or more internal solvent-filled chambers. The sample may then be delivered in liquid form to the channel(s) for analysis.

In some embodiments, the channels are constructed and arranged for essentially simultaneous analysis of a sample introduced into the inlet, where each channel comprises a different chemical reagent that interacts with a particular analyte, if present, to produce a determinable signal. Some chemical reagents may be selected to produce a signal upon interaction with a range of analytes, while some chemical reagents may be selected to produce a signal only upon interaction with a specific analyte. In some cases, it may be desirable to load the chemical reagents onto the device (e.g., within channels) dry until use in order to enhance stability and/or shelf-life. For example, the chemical reagent may be in substantially solid form or may be at least encapsulated by a solid material (e.g., a gel capsule).

In some embodiments, the channel(s) may include additional features which facilitate analysis of the sample. For example, the channel(s) may include one or more reaction wells. In some cases, a channel may include one reaction well containing a chemical reagent, such that a one-step chemical reaction or interaction occurs upon contact between the sample and the chemical reagent within the reaction well. For multistep reactions, the channels may be designed to introduce additional features to increase residence time and mixing. In some cases, a channel may include more than one reaction well for multi-step chemical reactions or interactions. For example, a channel may include a first reaction well containing a pre-treatment reagent and a second reaction well containing a chemical reagent, where the second well is positioned downstream from the first reaction well. For example, the detection of nitrate esters and nitramines via the Griess reaction is a multi-step reaction requiring pre-treatment with base, followed by diazotization with sulfanilamide under acidic conditions, and reaction with N-(1-naphthyl)ethylenediamine to generate the azo dye. To accomplish this, a first region of the channel may be coated, or otherwise loaded, with a base (e.g., a pre-treatment zone). A second region of the channel downstream from the first region may then be loaded with the remaining reagents needed to generate the azo dye (e.g., the reaction zone).

In some cases, the channel may be designed to expose the sample to multiple chemical reagents. For example, a channel may include a first reaction well containing a first reagent and a second reaction well containing a second chemical reagent, where the second well is positioned downstream from the first reaction well. In such embodiments, a sample within a single channel may be evaluated by more than one colorimetric or luminescent test for determination of any analyte(s) present.

The channel(s) may also include a mixing region or mixing chamber positioned downstream from the reaction well, and a detection well positioned downstream from the mixing region, wherein the luminescent or colorimetric signal is determined within the detection well. In some cases, the detection well(s) may be constructed such that fluid flow to the detection well may cease once the detection well(s) are full, allowing other detection wells to receive sample and thereby produce results. For example, the detection well(s) may include a gas-permeable film positioned over the exit. In some embodiments, the channel(s) can include a waste reservoir positioned downstream from the detection well. In some cases, the channel(s) may also include a de-bubbling region or chamber for reducing or eliminating, for example, air bubbles from the flow of sample. This may be useful preventing air bubbles from entering the reaction and/or detection wells, where they may potentially disrupt or obstruct device performance. The de-bubbling chamber may include a gas-permeable layer such as PFTE or other materials that are compatible with the device. In one embodiment, the de-bubbling chamber may include PTFE as a gas-permeable membrane, which may be heat-welded, attached by adhesive, or otherwise incorporated within the device, to form a seal.

Figure 13:
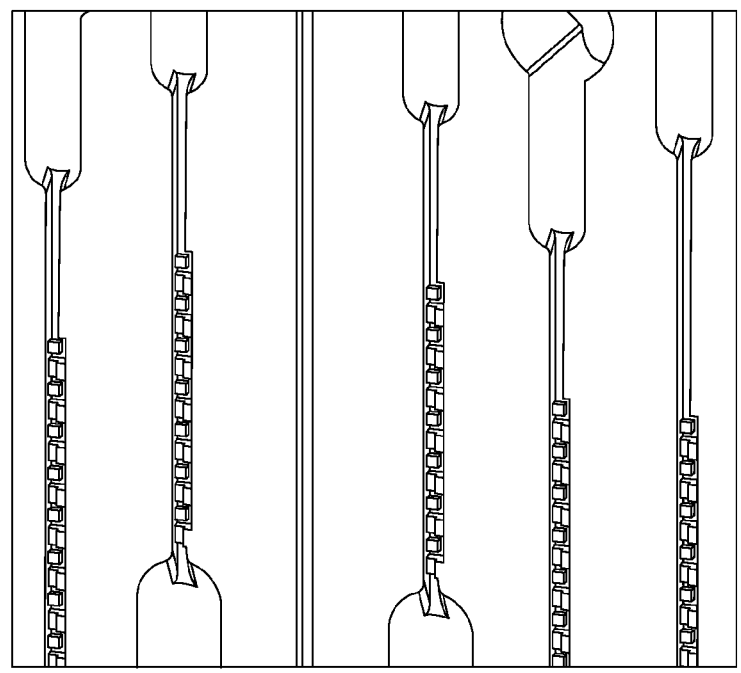
FIG. 13 shows view of an exemplary microfluidic channel containing a pathway that changes x, y, and z direction abruptly and repeatedly to reduce or prevent laminar flow.
Figure 13:
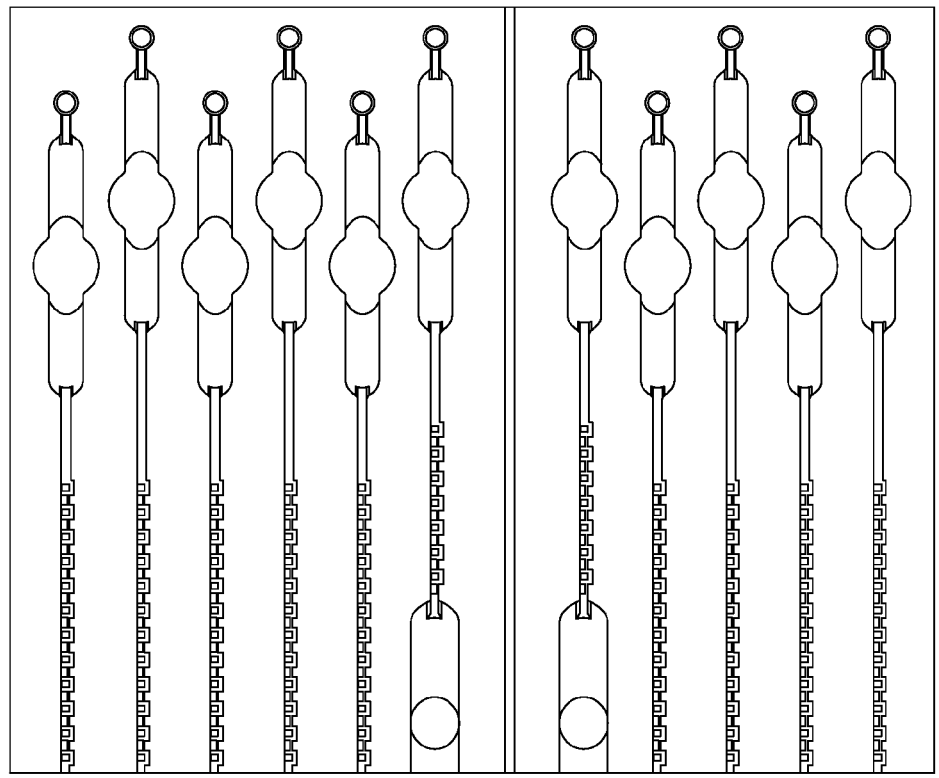

Various factors may be considered when designing and selecting a sample analysis device or sample analysis portion suitable for a particular application, including microfluidic channel architecture (e.g., channel dimensions and surface treatments), strategies for pre-loading the detection chemistries, techniques to optimize contrast and visibility of the colorimetric and/or luminescent signals (e.g., white backgrounds, reflective coatings, incorporation of scattering media, feature size/layout), and manufacturability. For example, the microfluidic channel(s) may be constructed to reduce or prevent laminar flow, for example, by forming a non-linear pathway having a direction that repeatedly changes in its x, y, and z directions, as shown in FIG. 13. In some cases, the direction change may be abrupt, such as a 90-degree change in direction. In some cases, the non-linear pathway forms a substantially serpentine, substantially S-shaped, or a substantially spiral pathway. Such microfluidic channel(s) are described in Vijayendran et al., "Evaluation of a Three-Dimensional Micromixer in a Surface-based Biosensor," Langmuir 2003, 19, 1824-1828, the contents of which are incorporated herein by reference in its entirety for all purposes.

Various analyte detection chemistries may be employed in the embodiments described herein. In some cases, the chemical reagent may be a luminescent or colorimetric reagent. That is, the chemical reagent may produce a determinable luminescent or colorimetric signal upon interaction with a particular analyte. In some cases, the determinable signal comprises a plurality of luminescent or colorimetric signals (e.g., a "barcode" of signals).

In some cases, a colorimetric reagent may be utilized. Some advantages of utilizing colorimetric detection include rapid analysis, high sensitivity, visual results interpretation, low cost, and the ability to detect and identify of trace levels of explosives and explosives residues (pre- or post-blast). Typically, colorimetric reagents generate a new chromophore upon interaction with an analyte, such that visible color changes through chemical reactions may indicate the presence of an analyte. Examples of such chemical reagents and reactions include, but are not limited to, Meisenheimer complex formation, the Griess reaction. For example, some nitroaromatics undergo nucleophilic aromatic substitution reactions with strong bases to form highly colored adducts (e.g., Meisenheimer complexes), with specific substituent differentiation based on the resultant color. The Griess reaction may be used to detect nitrite anions. Nitrate esters or nitramines may be treated with a base to generate nitrite anions, diazotized with sulfanilamide under acidic conditions, and reacted with aromatic amines (e.g., N-(1-naphthyl)ethylenediamine) to generate highly colored azo dyes. This reaction can also be used to detect inorganic nitrates, following Zn reduction to nitrite. Other examples of colorimetric reagents are shown in Table I below.

TABLE I

Detection chemistries.

| HME Precursor | Colorimetric Test | Cross-Reactivity |
|---|---|---|
| Chlorate | Aniline sulfate reagent | Chlorate |
| Perchlorate | Chloric acid test | Chlorate, chloric acid, periodate, persulfate |
| | Phenylanthranilic acid test | Chlorate, chloride, perchlorate |
| Nitramine Nitrate ester | Dichlorofluorescein reagent | HMX, PETN, RDX |
| | RDX test (J-acid) | Formaldehyde, RDX |
| | RDX test (thymol) | HMX, RDX |
| Nitrate | Alvarez's reagent | Nitrate, Nitrite |
| | Nitrate test (Gutzeit scheme) | Nitrate |
| | Safranin T solution | Nitrate, Nitrite |
| Nitroaromatic | Janovsky test | DNT, TNT |
| | Nitrotoluene test | DNT, NT, TNT |
| | Trinitrotoluene test | DNT, TNT |
| Permanganate | Diphenylamine indicator solution | Dichromate, hypochlorite, nitrate, nitrocellulose, oxidizers, permanganate |
| Peroxide | Potassium iodide starch test | Chlorine, hydrogen peroxide, iodine |
| Al | Aluminon reagent | Aluminum, beryllium, cerium, iron, thorium, zirconium |
| | Quinalizarin reagent (aluminum) | Aluminum, beryllium |
| Mg | Diaminobenzene solution | Magnesium |

In some cases, orthogonal detection chemistries can be incorporated to reduce occurrence of false positives and/or misidentification of analyte identity and the detection chemistries may be changed as new target analytes emerge. In some cases, multiple orthogonal detection chemistries (e.g., 5 or more, 10 or more) may be employed simultaneously. By the appropriate choice of detection chemistries, the devices or portions can be tailored towards the detection of a wide range of analytes as described herein.

Differentiation between analytes can be achieved by expanding both the number and types of chemical reagents involved, revealing the forensic "fingerprint" of the sample. While some chemical reagents are broad in scope and interact with many analyte classes (e.g., diphenylamine test), some respond to only one class of analyte (e.g., Meisenheimer test) and others are analyte-specific (e.g., p-DMAC test). For example, the ability of multiplexed reactions to positively identify analytes can be illustrated by the fact that it is possible to discern among urea, ammonium nitrate (AN), and urea nitrate (UN) using a combination of Zn-modified Griess and p-DMAC reactions. A color change in the Zn-modified Griess reaction can identify the inorganic nitrates (AN and UN), while a color change in the p-DMAC reaction can distinguish between UN and AN. For a definitive AN identification, an ammonium test may be used as well.

Use of orthogonality in the detection chemistries can aid in mitigating any deleterious effects by interferents and effects of under-sampling or over-sampling. Other factors that can be considered in minimizing such deleterious effects include controlling the surface area of the rolling substrate to limit the amount of sample collected, and utilizing chemistries with well-defined end-points that may not bleach out upon over exposure to analyte.

Figure 6:
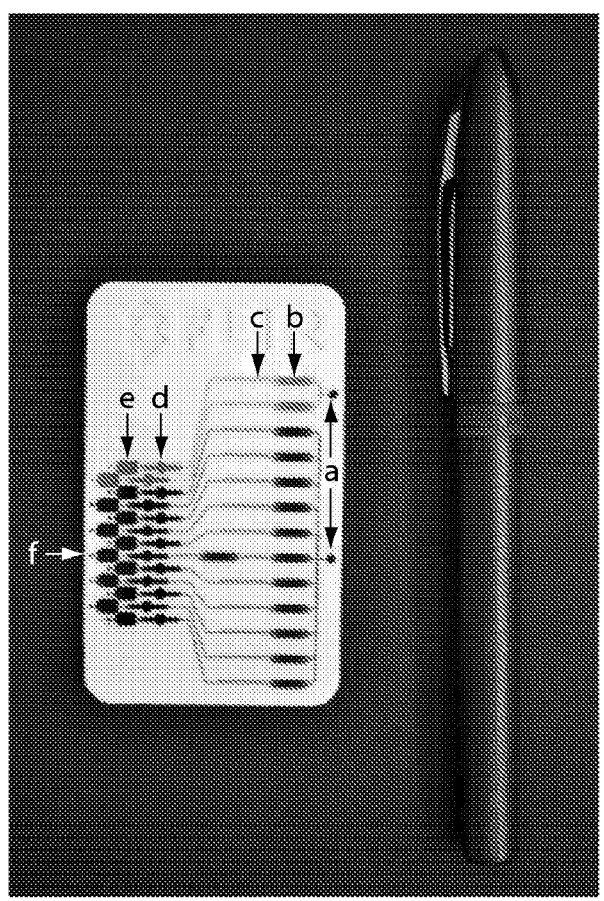
FIG. 6 shows a photograph of an analysis subcomponent of a device as described herein.

FIG. 6 shows a photograph of a prototype sample analysis device including (a) sampling ports, (b) reaction wells pre-loaded with chemical reagents, (c) mixing channels, (d) detection wells, (e) waste reservoirs, and (f) nitrate ester and nitramine channel. The top two sampling ports may be for metals detection, such as aluminum and magnesium detection, and are designed to accept about 50 microliters of fluid sample. The remaining 11 sampling ports may be for other analytes such as nitroaromatics, nitrate esters and nitramines, inorganic nitrates, chlorates, perchlorates, permanganates, and PBEs, and are designed to accept about 275 microliters of fluid sample. The prototype sample analysis device was fabricated in polypropylene using soft embossing techniques. The detection wells may be specifically designed micro-cuvettes optimized for maximum color intensity and contrast. The nitrate ester and nitramine channel was designed to accommodate a multistep reaction requiring pre-treatment with, for example, base prior to performing the Greiss detection chemistry, as described herein.

Figure 11:
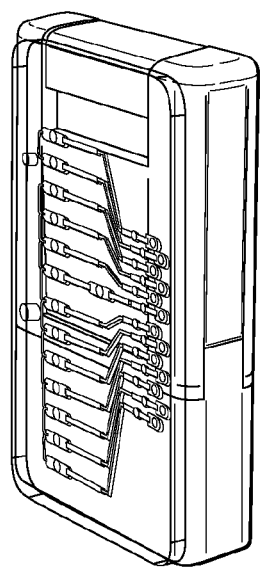
FIG. 11 shows a mock-up of a device for determining an analyte, according to one embodiment.

In some embodiments, a sample collection device and a sample analysis device may be provided together in a kit. FIG. 11 shows an illustrative embodiment of a kit containing both a sample collection device and a sample analysis device. For example, the sample collection device may be designed to be snapped into a sampling port of the sample analysis device, and the fluid sample transferred from the sample collection device into the reaction zone of the sample analysis device that is pre-loaded with detection chemistries. In some cases, the device may display the analysis results ~1 minute later. The design may also retain an archival sample (unreacted) for subsequent forensic testing. For example, the device may contain an additional roller.

Figure 2A:
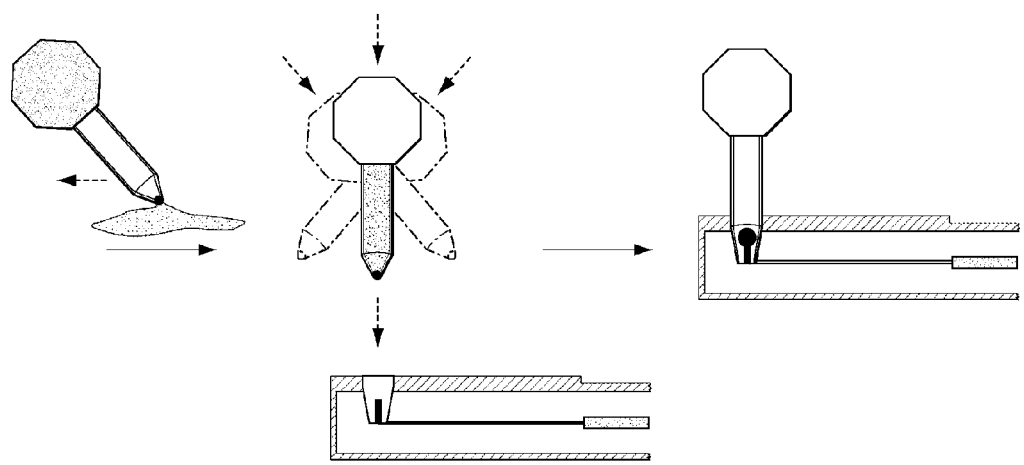
FIG. 2 shows a method for determination of an analyte including (a) sample collection and (b) sample analysis.
Figure 2B:
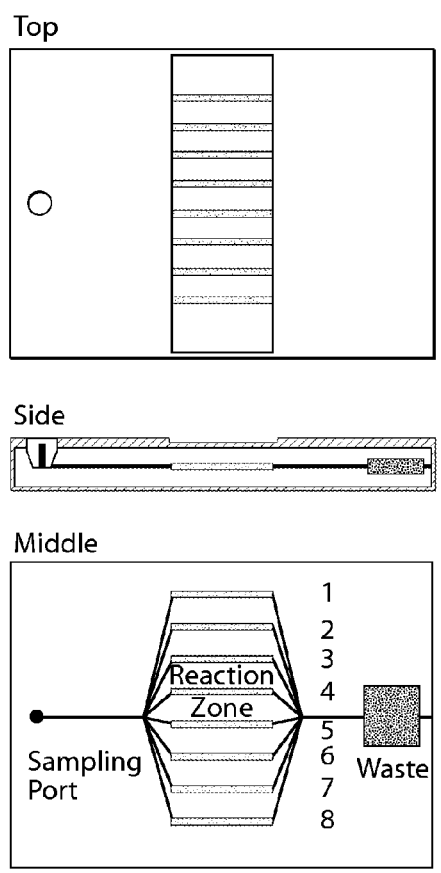

An illustrative embodiment of an overall assay scheme using a sample collection device and a sample analysis device as described herein is shown in FIG. 2. As shown in FIG. 2A, the sample may be swiped with the sample collection device, collecting sample on a rolling substrate, and an internal solvent chamber is crushed to release solvent. The sample collection device may be shaken (e.g., for about 5-10 seconds) to form a fluid sample and the sample collection device may then be snapped into the sample analysis device, releasing the sample. The fluid sample may travel into the reaction zone, pre-loaded with the detection chemistries and resultant color changes (positive results) can be observed ~1 minute later to identify any explosives or other analytes present. (FIG. 2B) This combined assay may enable class-level identification of homemade explosives or explosive precursors such as nitroaromatics, nitrate esters and nitramines, inorganic nitrates (including fertilizer-based explosives), chlorates, perchlorates, peroxide-based explosives (PBEs), gun powder or gun-shot residue, and other controlled substances, in a convenient single-use device.

In another set of embodiments, a sample collection portion and a sample analysis portion may be integrally connected to one another within a single device. As used herein, the term "integrally connected," when referring to two or more objects, means that the objects that do not become separated from each other during the course of normal use, e.g., separation requires at least the use of tools, and/or by causing damage to at least one of the components, for example, by breaking, peeling, dissolving, etc. The sample collection portion and sample analysis portion may be arranged in fluid communication with one another such that sample from the sample collection portion may be delivered or transferred to the sample analysis portion during operation.

In some embodiments, the sample collection portion and the sample analysis portion may be arranged on the same side of the device. For example, the sample collection portion may be arranged on a first region of the device and the sample analysis portion may be arranged on a second region of the device, where the first and second regions are located on the same side of the device. In some embodiments, the sample collection portion and the sample analysis portion may be arranged on different sides of the device (e.g., the first and second regions are located on different sides of the device). For example, the sample collection portion may be arranged on a first region of the device and the sample analysis portion may be arranged on a second region of the device, where the first and second regions are located on opposing sides of the device, or, on sides which are substantially perpendicular to one another. In some embodiments, the device may include a first side on which the sample collection portion is arranged, and a second, opposing side on which the sample analysis portion is arranged. It should be understood that the sample collection portion and the sample analysis portion may be arranged in any configuration suitable for a particular application.

FIG. 12 shows an illustrative embodiment of a device including a sample collection portion and a sample analysis portion arranged on opposing sides of a single device. FIG. 12A shows the front side on which the sample analysis portion is arranged, and FIG. 12B shows the rear side on which the sample collection portion is arranged. In this embodiment, the sample collection portion includes two sample collection pads or substrates: sample collection substrate I is arranged in fluid communication with, and directly behind, the mixing chamber of the sample analysis portion. (FIG. 12B) Sample collection substrate I may be used for collection and immediate analysis of the sample. Sample collection substrate II is optional and may be used to store the sample, for example, for subsequent confirmatory lab testing. The sample collection substrates may be integrally connected to the device, or may optionally be detachably attached to the device (e.g., may be detached from the device during sampling, then reattached for sample analysis). The sample collection substrates may be arranged within sample collection wells arranged directly on the surface of the device, as shown in FIG. 12B.

Figure 12A:
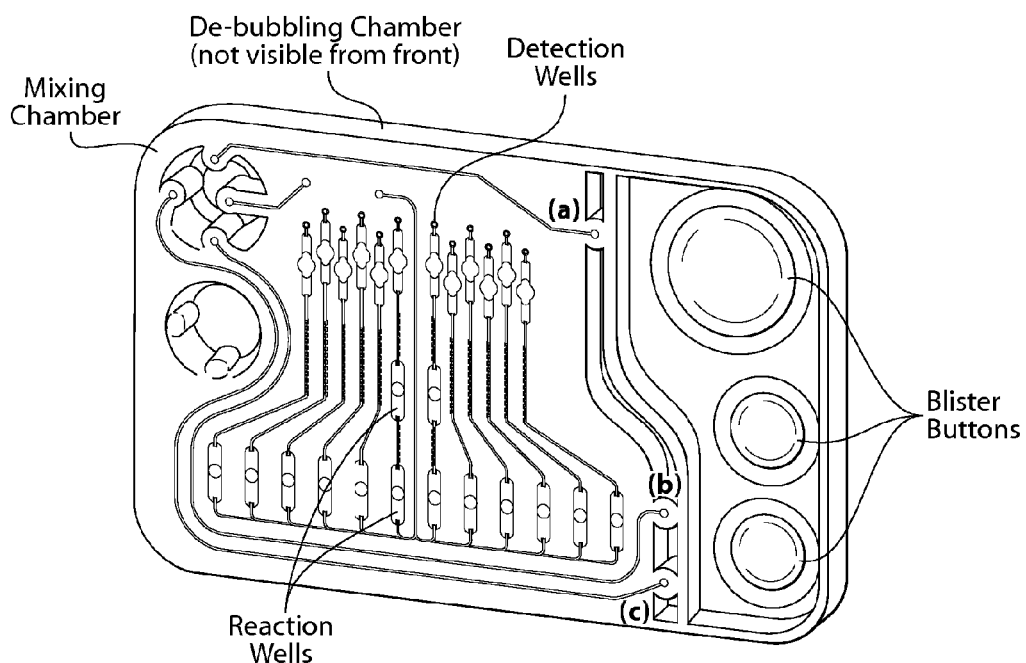
FIG. 12 shows various regions of a device for determining an analyte, including (a) a sample analysis portion on a first side of the device, (b) a sample collection portion on a second, opposing side of the device, (c) (i) three-dimensional and (ii) two-dimensional view of the sample collection portion, (d) an exemplary sample collection substrate, and (e) view of the sample analysis portion (i) without the analysis cover and (ii) with the analysis cover.
Figure 12B:
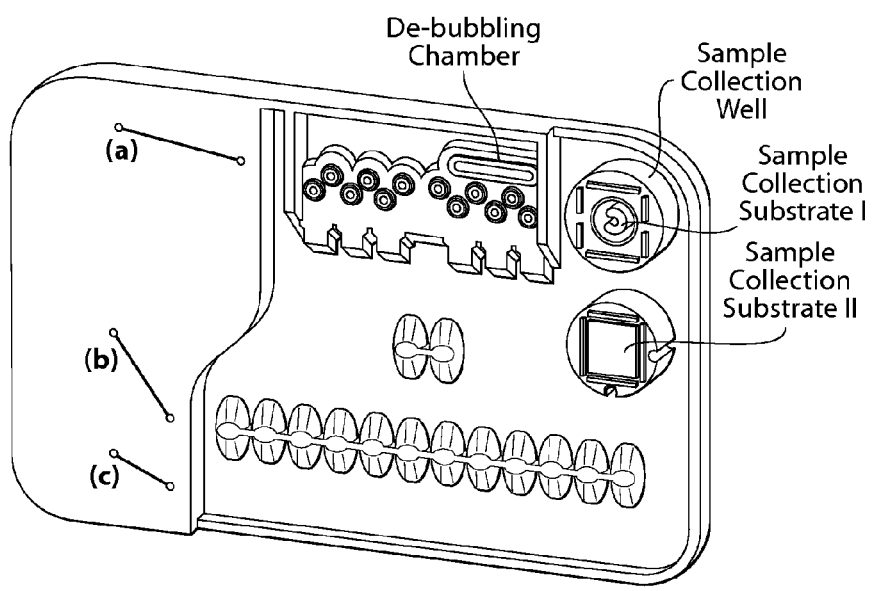
Figure 12C:
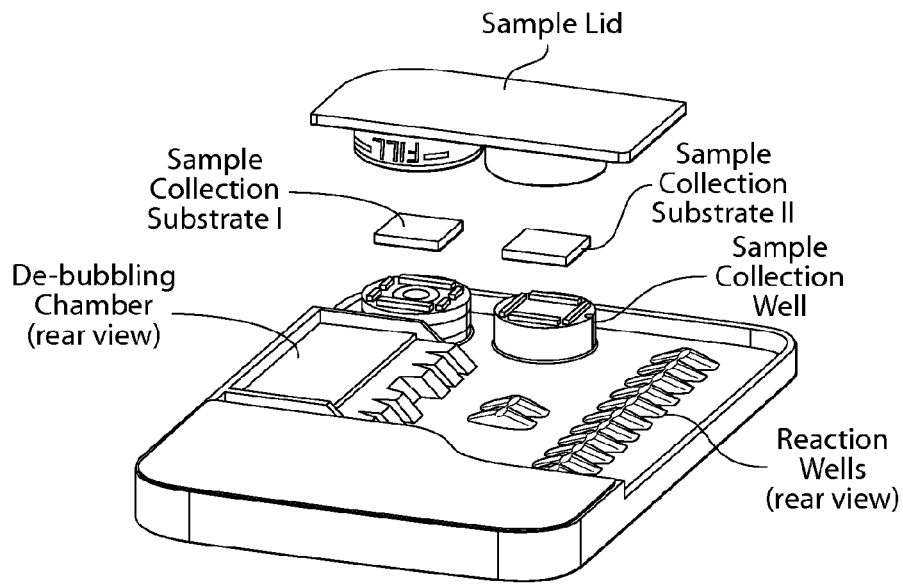
Figure 12C:
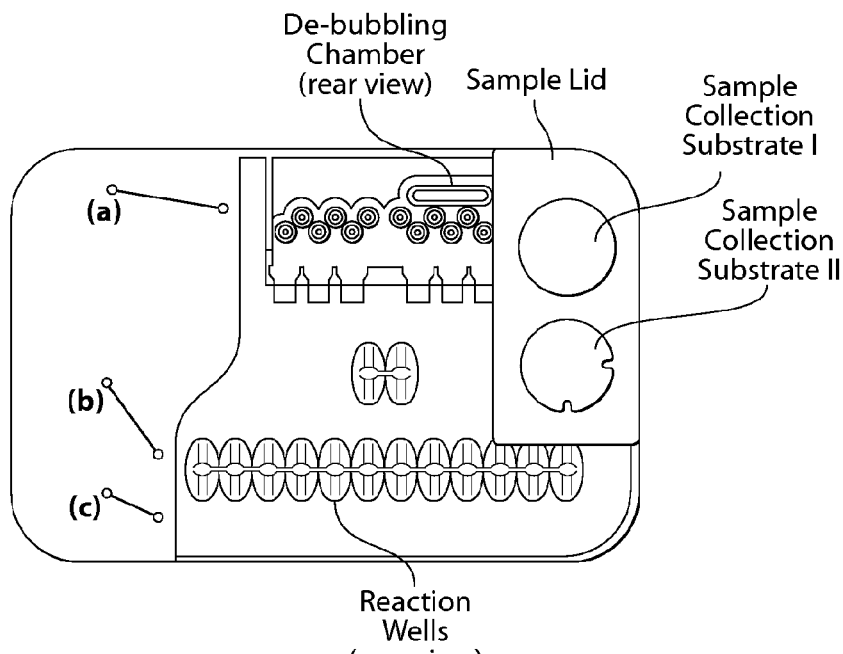
Figure 12D:
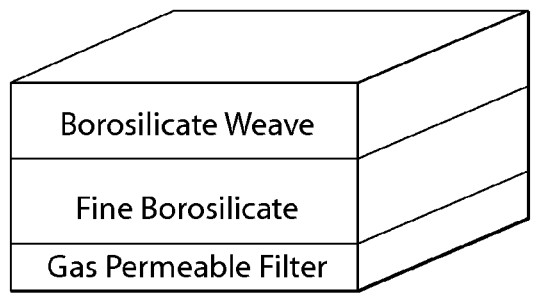

FIG. 12C shows another view of various components of the sample collection device, including a sample lid that can protect the sample collection substrates from premature contamination and that can also act as a plunger having a first position and a second position lower than the first position. In operation, the lid can be used to facilitate transfer of the sample from the sample collection substrate to the mixing chamber of the sample analysis device, as described more fully below. The sample collection substrate utilized in this embodiment includes a fine borosilicate material (1 µm pore size) arranged between a borosilicate weave (10 µm pore size) and a gas permeable filter comprised of PTFE, as shown in FIG. 12D. This sample collection substrate is shown by way of example only, and it should be understood that other materials may be suitable for use as a sample collection substrate.

Figure 12E:
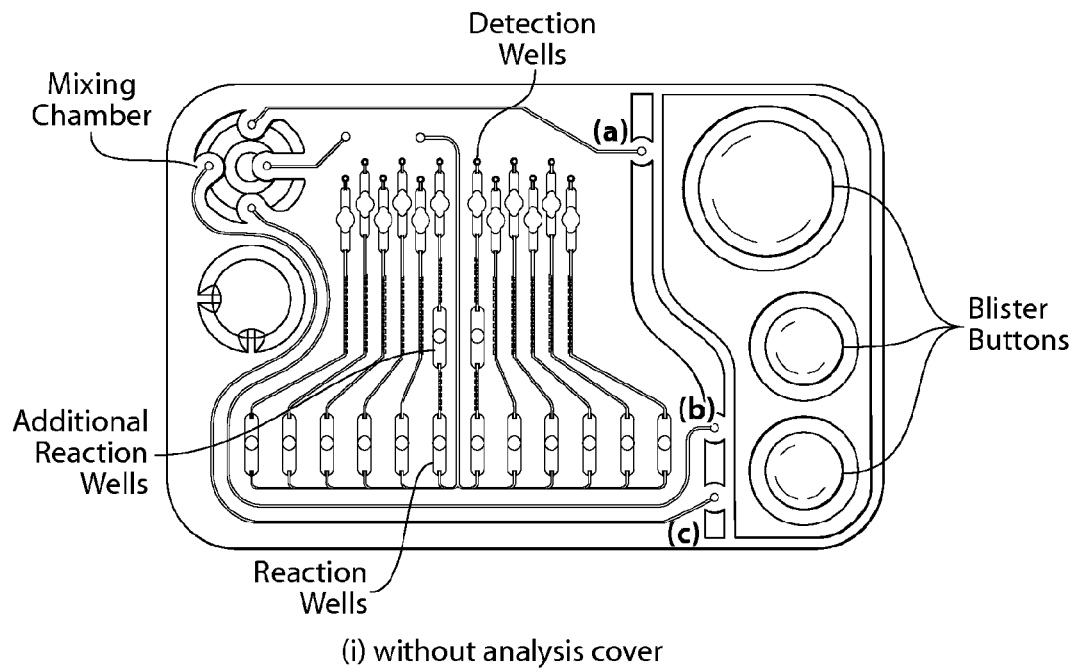
Figure 12E:
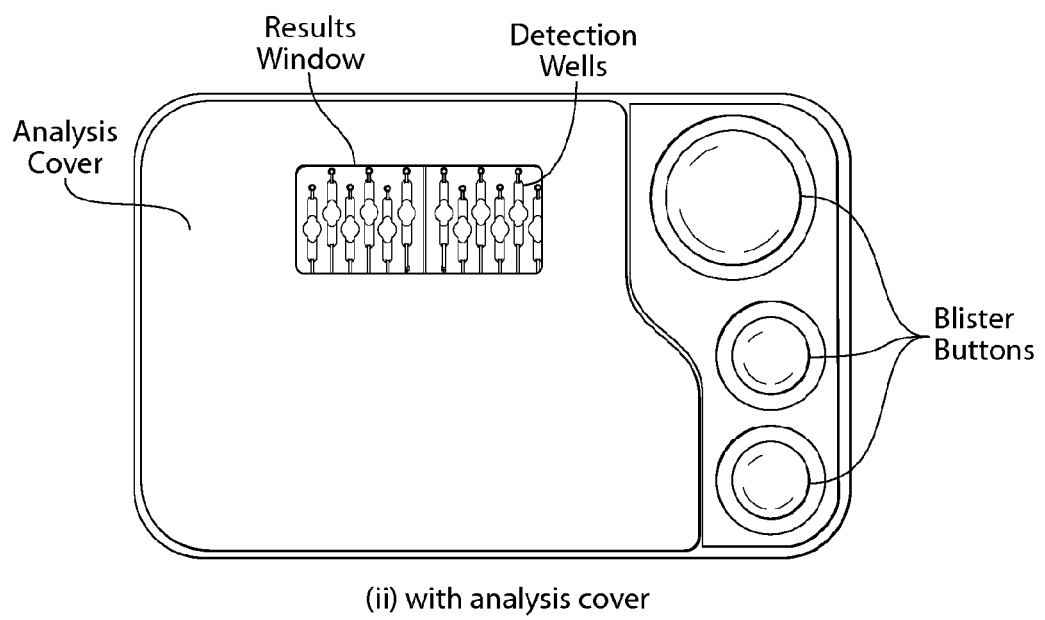

FIG. 12A shows a three-dimensional view (while FIG. 12E(i) shows a two-dimensional view) of the sample analysis portion of the device, including a microfluidic system with various regions in fluid communication with one another, such as a mixing chamber arranged to receive sample from the sample collection substrate, a de-bubbling chamber, and a plurality of reaction wells and detection wells as described herein. In the embodiment shown in FIG. 12A, the mixing chamber may be in fluid communication with the de-bubbling chamber (not visible in FIG. 12A) which may connect the mixing chamber to the plurality of reaction chambers. In some cases, it may be desirable to construct and arrange the channel(s) to include multi-turn pathways between the reaction wells and the detection wells, thereby reducing or eliminating laminar flow. Additionally, one or more containers (e.g., "blister buttons") in which various solvents may be stored (e.g., for extraction or reaction with the sample on the sample collection substrate) may be arranged within the sample analysis portion. As shown in FIGS. 12A, 12B, 12C, and 12E, three solvent-filled "blister buttons" may be arranged in fluid communication with the mixing chamber via microfluidics pathways (a), (b), and (c). The device may further include an analysis cover which may be detachably attached to the sample analysis portion, as shown in FIG. 12E(ii). When assembled, the analysis cover may conceal substantially all of the sample analysis portion except for the plurality of detection wells, which may be viewed in a results window provided by the analysis cover.

In one set of embodiments, the device in FIG. 12 may be provided with the sample lid and the analysis cover detachably attached to the device. To analyze a solid sample, the sample lid may be removed and the sample collection substrates may be exposed to the substance or surface to be tested. The sample lid may then be re-attached and the device may be flipped over such that the sample analysis portion is visible. The three "blister buttons" may contain liquid solvents (e.g., the same solvent, or a set of different solvents) that, when the "blister button" is pressed, may be released and/or forced into the mixing chamber via the relevant microfluidic pathway (e.g., pathway (a), (b), or (c)). Depending on the test protocol for the particular device, instructions for the desired order of blister button actuation can be noted, for example, on a device label. In some cases, a first "blister button" may be pressed to release solvent, and the device may be agitated (e.g., shaken by hand) such that the solvent contacts the sample collection substrate and dissolves the solid sample material on the sample collection substrate, producing a liquid sample containing the analyte, if present, within the sample collection well. A second "blister button" may then be pressed to release additional or another solvent, and the device may again be agitated. A third "blister button" may be pressed to release additional or another solvent, and the device may be agitated further. The sample lid may then be pressed down (e.g., to a lower or "plunged" position) to force the dissolved sample (i.e., the sample combined with solvent(s) from the "blister button(s)") through the microfluidic system containing reaction wells and detection wells. The device may then be placed with the sample analysis portion facing up and the user may await the results by viewing the results window.

Upon combination of the sample and solvent(s) in the mixing chamber, the dissolved sample may pass through the de-bubbling chamber to the reaction wells, where the sample may or may not react with reagents positioned within the reaction wells. The reacted/unreacted sample may then travel along the channel to the detection wells, which may have an exit that is covered by a gas-permeable membrane. The gas-permeable membrane may allow any gas ahead of the liquid sample to exit the channel but may hold the liquid sample in place halting the flow. This may reduce or prevent extra liquid sample from entering the fastest-filling channels and may urge the remaining sample through the slower-filling channels.

It should be understood that the testing of solid samples using devices disclosed herein is discussed by way of example only. In any of the embodiments disclosed herein, the device may be adapted to accommodate the testing of vapor-phase samples and/or liquid-phase samples. In some cases, the sample collection substrate may include material(s) capable of concentrating and/or filtering a vapor sample. For example, the sample collection substrate may include a gas-permeable filter (e.g., PFTE membrane) and a preconcentrator material, such as glass wool, ceramic, Teflon®, glass filters, and other materials described in *Forensic and Environmental Detection of Explosives* (John Wiley & Sons, 1999); *Modern Methods and Applications in Analysis of Explosives* (John Wiley & Sons, 1996); and U.S. Pat. No. 8,307,724, the contents of which are incorporated herein by reference for all purposes. Sample analysis may then proceed as disclosed herein.

In some cases, the sample lid may be configured to have one or more features (e.g., trenches, containers, cups, etc.) arranged to receive and contain a liquid-phase sample, which may then be placed in contact with a sample collection substrate as disclosed herein. In some cases, the sample lid may be physically separated from the device and may include one or more empty sample collection wells (or other chambers) arranged on the sample lid such that, upon filling the sample collection wells with liquid-phase sample and assembling the device on top of the lid, e.g., sample collection portion side down, the liquid-phase sample may contact the sample collection substrates. In some embodiments, sample collection wells may be arranged directly on the device, with sample collection substrates positioned within the sample collection wells. The sample lid may be physically separated from the device to reveal the sample collection substrates within the sample collection wells, and a liquid sample may be added directly into the sample collection wells, contacting the sample collection substrates. The sample lid may then be re-attached to the device, enclosing the liquid sample within the sample collection wells. Optionally, one or more "blister buttons" containing solvent may be included within the device in order to provide additional solvent to be combined with the liquid sample. Sample analysis may then proceed as disclosed herein.

The sample analysis device or sample analysis portion may be fabricated using various known techniques. Once fabricated, the microfluidic device may be loaded with the individual detection chemistries and sealed. The chemical reagents can be deposited into the channels either directly, e.g., physically dried onto the walls of the channel, or indirectly, e.g., preloaded and dried onto a solid support such as silica gel, aluminum oxide, filter membrane, glass wool, etc. In some cases, non-volatile and/or liquid reagents may be employed. In some cases, barriers such as semi-permeable membranes and plugs can be incorporated into the design to prevent physical movement of the components (e.g., silica gel). Degradation of the chemical reagent may be minimized or prevented by, for example, storing them dry until use, avoiding the use of volatile reagents, utilizing robust chemistries not prone to decomposition, and/or incorporating physical barriers.

In some cases, poly(dimethylsiloxane) (PDMS) may be used for rapid prototyping and testing of the analysis cassette's design. In some cases, the device may be fabricated from injection-molded polypropylene or similar materials. The shelf-life of the sample analysis device may be assessed as a function of time, temperature, and humidity; in both real-time and accelerated (elevated temperatures and humidity) studies. Various screening tests may be employed to determine device performance. For example, the device may be challenged with a known mixture of analytes (e.g., explosives) and the results of individual assays may be analyzed colorimetrically. If any degradation in performance is observed, the contents of the degraded channels may be extracted and analyzed using standard analytical techniques (e.g., HPLC, GC-MS, and NMR) to determine the root cause of any degradation.

Various methodologies for analyzing the response of the device towards a particular sample may be utilized. For example, the resulting pattern of luminescent and/or colorimetric responses within a single device may provide a "barcode" or "fingerprint" specific to a particular analyte. In some cases, the barcode is read manually. In some cases, the barcode is read automatically. In some cases, orthogonal detection chemistries that exhibit binary color changes (e.g., colorless to red/blue/black) upon reaction with analytes can be used, thereby enabling manual and automated results interpretation. Regardless of the approach selected, hardware and software that are portable, simple to use, seamlessly integrated, and able to provide unambiguous results, may be utilized.

In some cases, the resulting signal from the device may be read manually. In this case, an end-user may observe the results by visual inspection and consult a reference table of indicator combinations and their corresponding explosive type to determine the analyte. In some cases, a decision tree may be used to analyze the results obtained from visual inspection of used differentiating devices, and the end-user may determine if a response had occurred for each reaction channel and input this binary data into the decision tree.

In some embodiments, the resulting signal from the device is automatically read. For example, the resulting barcode can be scanned and read using a camera-type device or application, e.g., on smart phones. In some cases, the barcode can be read as a simple number and interpreted based on tabulated data. Analysis software capable of deconvoluting the "fingerprint" response for each device response may be employed to analyze the barcode. For example, such software would convert the binary data (e.g., supplied by the end-user) into an analysis report indicating which, if any, analytes were present in the original sample. In some cases, a camera application, e.g., as found in cell phones or smart phones, may be used to scan or photograph the barcode and transmit the image to a central database for determining the identity of the analyte. For example, fiducial marks may be presented in the camera's viewer to guide in framing an image of the barcode. Once aligned with the marks, a virtual shutter may be snapped, causing an image to be captured. An algorithm may then resolve the barcode within the image, translating it to a universal product code (UPC) numerical sequence. The UPC may be identified to determine the analyte.

Alternative devices include single-pixel light sensors (across which the sample may be swiped) or bar code readers (that read a line across the results channels). For a chosen collection method, a system for aligning the image collector with the sample in X (alignment), Y (orientation), and Z (zoom/focus) coordinates. This can be accomplished with either the use of fiducial reference marks on the sample and collector or with the use of a jig to hold the collector and sample in a consistent relative position.

Based on the image collection method selected, a one-dimensional array of collected data or a one-dimensional "line scan" from within a two-dimensional image can be used. With a predetermined orientation and zoom for the scan and a known position and width for each analyte, the brightness threshold developed in the two-dimensional process can be used to determine whether a response occurred at each analyte position. This method allows creation of a table of analyte responses to the sample in question. In a two-dimensional method, images of the barcode can be captured and analyzed on a computer to define image and sample requirements. Responses for each analyte can be evaluated to determine a pixel brightness threshold that distinguishes between responses. This analysis can be conducted in both full color and grayscale. To simplify analysis, a universal threshold can be created for all reactions. Color and grayscale response of each analyte may be evaluated along the length/width of the reaction channel to determine the variability in response with position.

In some cases, software employing an algorithm that identifies the desired location on each reaction channel, compares the pixel brightness of each channel to the references and predetermined threshold, and reports and records the results, can be used. In such cases, a process that provides a repeatable indication across the variety of analytes and their differing responses is desirable.

In some cases, the resulting array of signals may be evaluated using an image-based analysis. For example, an algorithm incorporating routines for locating the various analyte stripes within the image, graphically determining the binary response of each analyte, and using a reference table to determine the various explosive constituents contained in the presented sample, may be employed. In some cases, the algorithm is compatible with current smart phones. In some cases, wireless (e.g., cell) communication may be used to transmit the image to a host computer for real-time analysis and display of results back on the fielded phone. In some cases, the image may be transmitted to a laptop, local to the sampling phone/camera, and image analysis and the subsequent display/recording of results may be performed. Because the algorithm would not reside in the phone in these cases, such an approach would be possible with any brand of phone containing a CCD camera with sufficient resolution and contrast.

As used herein, a luminescent signal or luminescent emission may be an emission of ultraviolet or visible radiation. Specific types of luminescent signals include fluorescence, phosphorescence, chemiluminescence, electrochemiluminescence, and the like. For example, the emission may be "chemiluminescence," which refers to emission of radiation due to a chemical reaction, or "electrochemiluminescence," which refers to emission of radiation due to electrochemical reactions. In some cases, the emission may be fluorescence emission. Those of ordinary skill in the art would be able to select various luminescent chemical reagents suitable for use in the invention.

Devices and methods described herein may be useful in the determination of a wide range of analytes including drugs (narcotics), chemical warfare (CW) agents, biological warfare (BW) agents, toxic industrial chemicals (TICs), toxic industrial metals (TIMs), gunshot residue, other controlled substances, and the like. In some embodiments, the devices and methods may be useful in water monitoring, i.e., determining analytes that may be present in water. In some cases, the analyte is an explosive, or precursor thereof. Examples of explosives include, but are not limited to nitroaromatic molecules (e.g., TNT, DNT), non-aromatic explosives such as RDX (hexahydro-1,3,5-trinitro-1,3,5-triazine), PETN (2,2-bis[(nitrooxy)-methyl]-1,3-propanediol dinitrate (ester)), ethylene glycol dinitrate (EGDN), tetryl, nitroglycerin, HMX, nitrate, chlorate, perchlorate, permanganate, peroxide-based explosive, Al, Mg, other nitro- or nitrate-containing species, precursors thereof, and the like. In some embodiments, the analyte is present in water.

In one set of embodiments, the analyte may be a drug. The drug may be, in some cases, a controlled substance. As used herein, the term "controlled substance" refers to any substance whose manufacture, possession, and/or use are regulated by a government. In some embodiments, the drug may be a controlled substance prohibited by governmental regulation. In some embodiments, the drug may be a controlled substance not prohibited by governmental regulation but may be diverted for illicit purposes. For example, the drug may be a controlled prescription drug diverted for illicit purposes (e.g., without prescription). Drugs may include narcotics such as heroin and oxycodone, stimulants such as cocaine and methamphetamine, depressants such as benzodiazepines, hallucinogens such as lysergic acid diethylamide (LSD), cannabis, "bath salts" containing amphetamine-like chemicals such as methylenedioxypyrovalerone, mephedrone and pyrovalerone, and the like. In some embodiments, the drug may be an amine-containing compound. In some embodiments, the drug may be a phenol-containing compound. Examples of drugs include, but are not limited to, tetrahydrocannabinol (or delta-9 THC) as found in marijuana, hashish, hashish oil, or cannabis, methamphetamine, amphetamine, crack cocaine, cocaine, heroin (including black tar heroin), 3,4-methylenedioxymethamphetamine (or Ecstasy), oxycodone, morphine, psilocybin, psilocin (as found in psychedelic mushrooms), lysergic acid diethylamide (LSD), hydrocodone, benzodiazepines, salts thereof, or mixtures thereof. It should be understood that the determination of drugs such as narcotics is described herein by way of example only.

As used herein, the term "chemical reagent" is given its ordinary meaning in the art and refers to a species added to a reaction mixture in order to produce a chemical reaction or chemical transformation of at least one component present in the reaction mixture. In some embodiments, the chemical reagent is consumed in the course of a chemical reaction. Solvents or fluid carrier are typically not referred to as "chemical reagents."

As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

EXAMPLES AND EMBODIMENTS

Example 1

The following example describes the study of sample collection efficiency using either a swipe or a roller. Analyte samples were prepared by dry transfer of the analyte to a cardboard or plastic substrate. To evaluate swipe collection efficiency, the analyte substrate was swiped with either Nomex™ or 3M™ tape, and the sample was extracted from the swipe by solvent and analyzed by HPLC and/or ion chromatography. To evaluate rolling substrate collection efficiency, a prototype roller was functionalized with a swipe material, e.g., Nomex™ or 3M™ tape, and contacted with the analyte substrate via a "one roll" swiping mechanism. The sample was then extracted from the roller by solvent (800 µL) and analyzed by HPLC and/or ion chromatography. The solvent mixture utilized in these tests was based on compatibility with the detection chemistries. Tests were repeated 5 times or more.

FIG. 4 shows a comparison of sample collection efficiency for either swiping or rolling contact with (a) RDX, (b) TNT, (c) nitrate salt, and (d) percholate salt, using either Nomex™ or 3M™ tape. Results for the rolling contact are the left columns, and results for the swiping contact are the right columns.

Example 2

Figure 3:
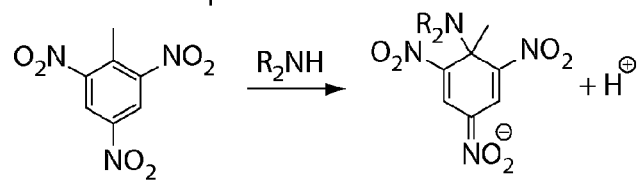
FIG. 3 shows various colorimetric chemical reactions useful in determining an analyte, including (a) the Meisenheimer complex formation, (b) Greiss reaction, (c) [Pt(typ)Cl]$PF_6$ perchlorate test, (d) hydrolytic boronate deprotection, and (e) complexation of urea nitrate with p-DMAC.
Figure 3:
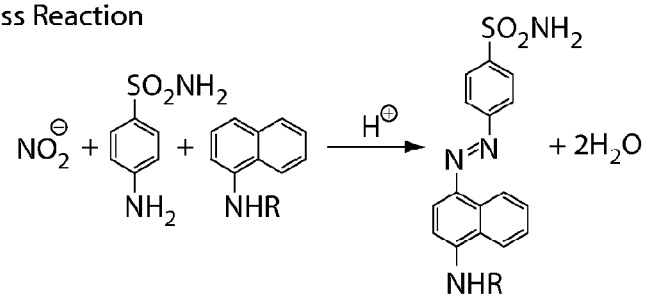
Figure 3:
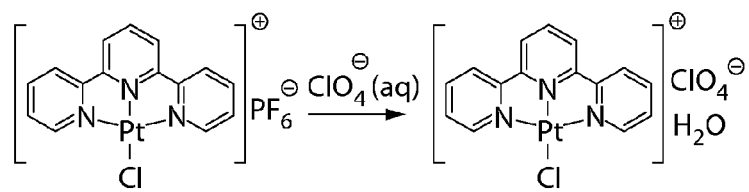
Figure 3:
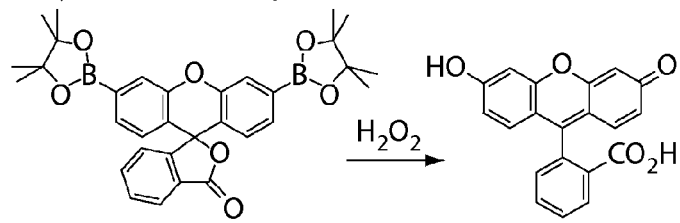
Figure 3:
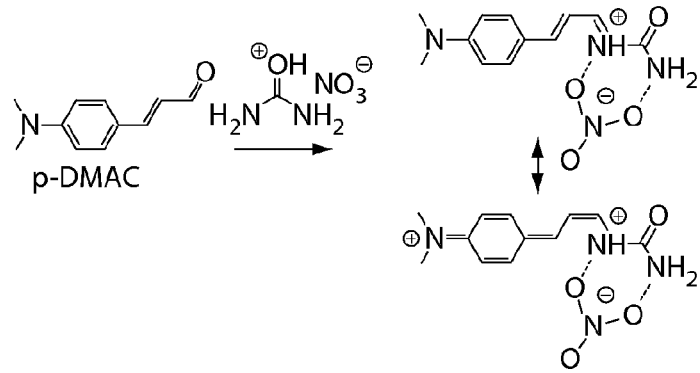
Figure 4A:
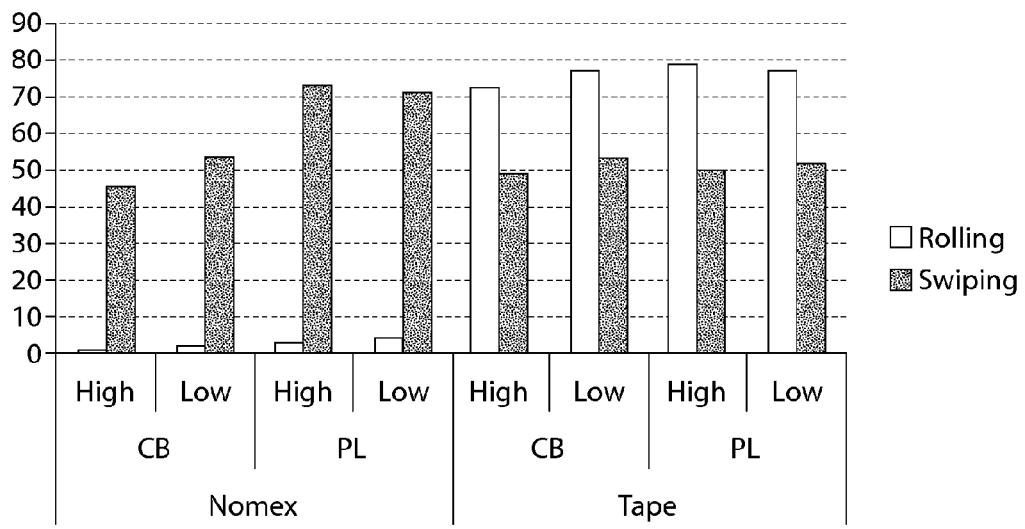
FIG. 4 shows a comparison of sample collection efficiency for either swiping (right columns) or rolling (left columns) contact with (a) RDX, (b) TNT, (c) nitrate salt, and (d) percholate salt, using either Nomex or tape.
Figure 4B:
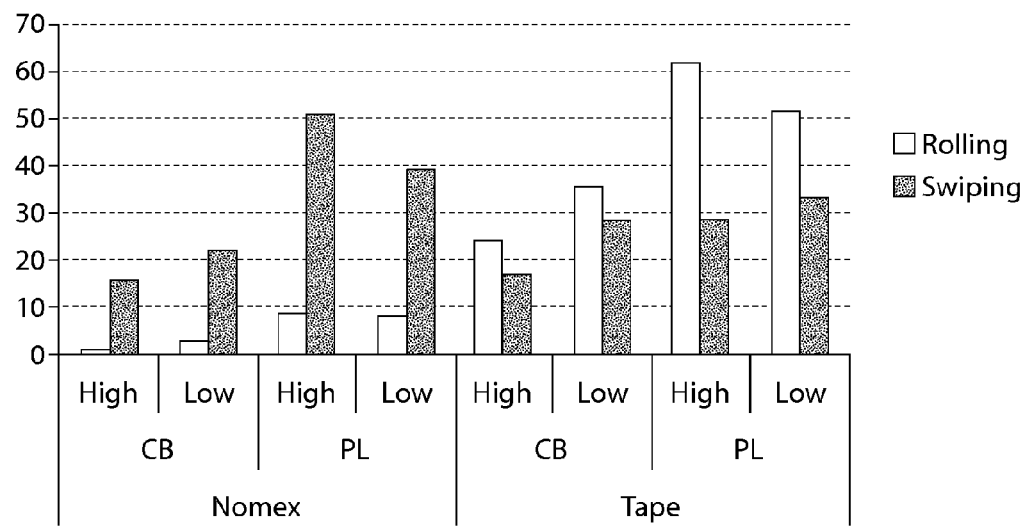
Figure 4C:
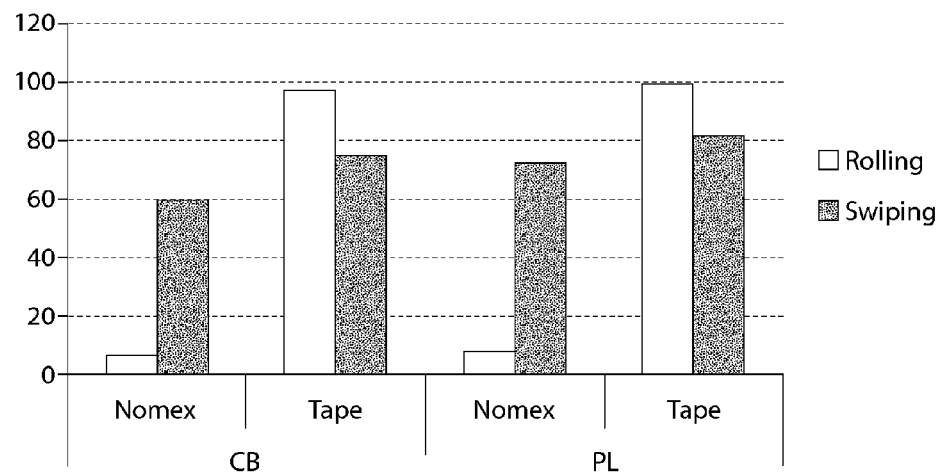
Figure 4D:
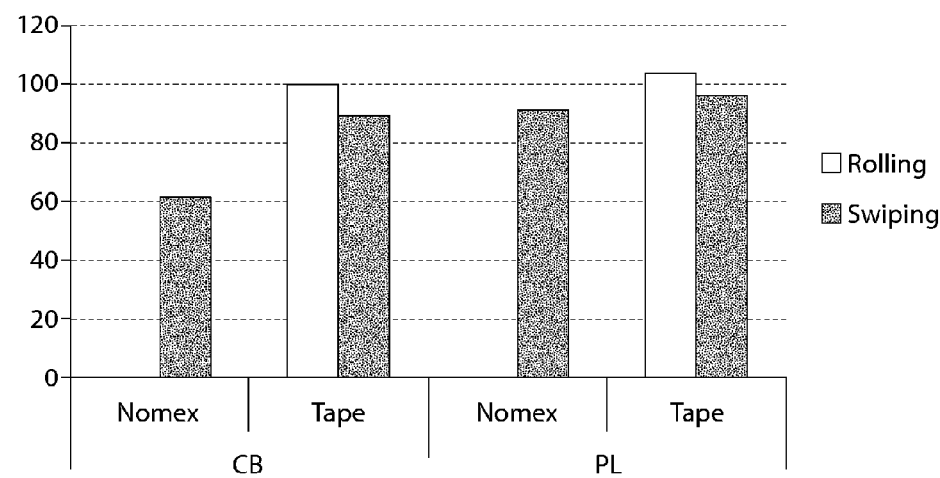
Figure 7A:
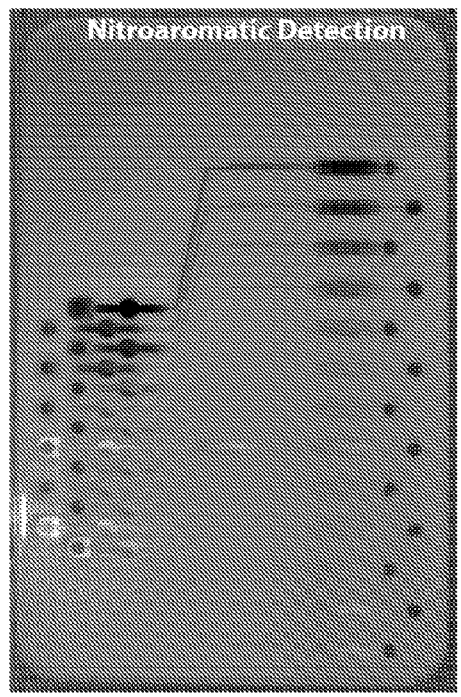
FIG. 7 shows photographs of the colorimetric response of a device upon exposure to (a) a nitroaromatic, (b) a nitrate, (c) ammonium, and (d) acids and bases.

The following example describes the determination of various analytes using devices as described herein. FIG. 7A shows the detection of a nitroaromatic using the formation of a Meisenheimer complex, as shown in FIG. 3A. A fluid sample containing trinitrotoluene (TNT) was injected into the prototype sample analysis device pre-loaded with Meisenheimer reagents, at various concentrations, with the results for the highest concentrated sample shown in the top channel.

Figure 7B:
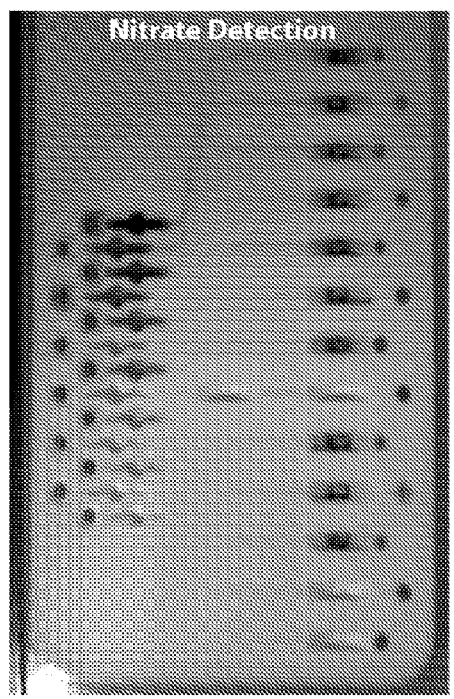

FIG. 7B shows the detection of an inorganic nitrate using the zinc-modified Griess reaction. A fluid sample containing an inorganic nitrate was injected into the prototype sample analysis device pre-loaded with zinc-modified Griess reagents, at various concentrations, with the results for the highest concentrated sample shown in the top channel.

Figure 7C:
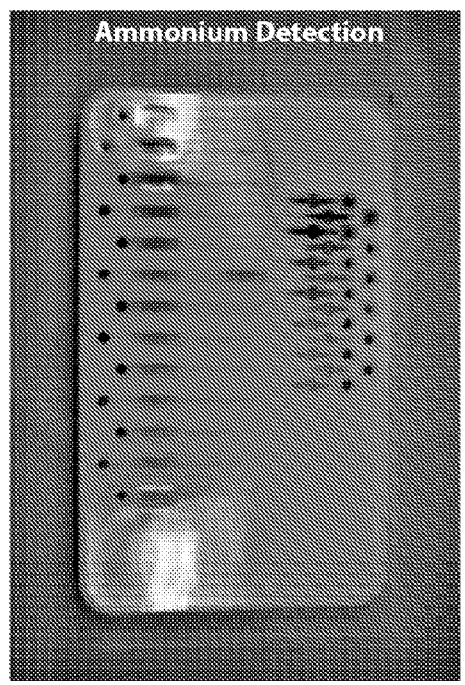

FIG. 7C shows the detection of ammonium nitrate using Berthelot's reaction. A fluid sample containing ammonium nitrate was injected into the prototype sample analysis device pre-loaded with Berthelot's reagents, at various concentrations, with the results for the highest concentrated sample shown in the top channel.

Figure 7D:
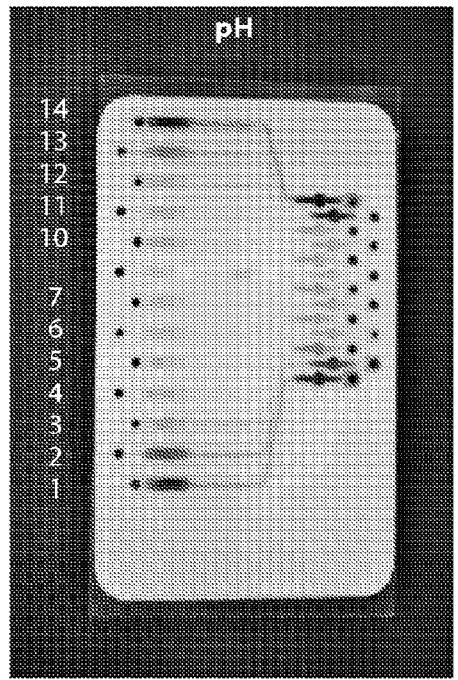

FIG. 7D shows the detection of acids and bases using a pH sensitive dye. A fluid sample containing acid or base was injected into the prototype sample analysis device pre-loaded with pH sensitive dye, at various pH's, with the results for the highest pH shown in the top channel.

Figure 8:
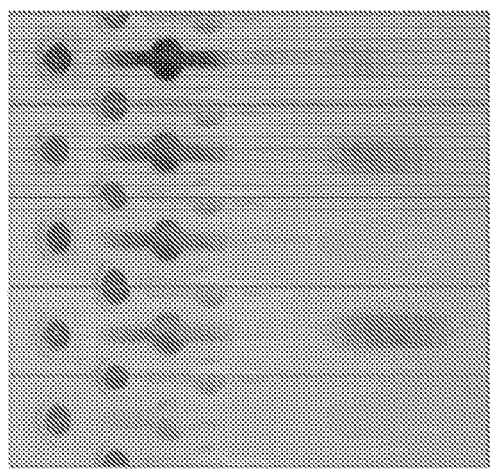
FIG. 8 shows a photograph of the colorimetric response of a device upon exposure to nitrate esters and nitramines.

FIG. 8 shows the detection of nitrate esters and nitramines via the multistep Griess reaction. A fluid sample containing RDX was injected into the prototype sample analysis device pre-loaded with base and Griess reagents, at various concentrations, with the results for the highest concentrated sample shown in the top channel.

Figure 9:
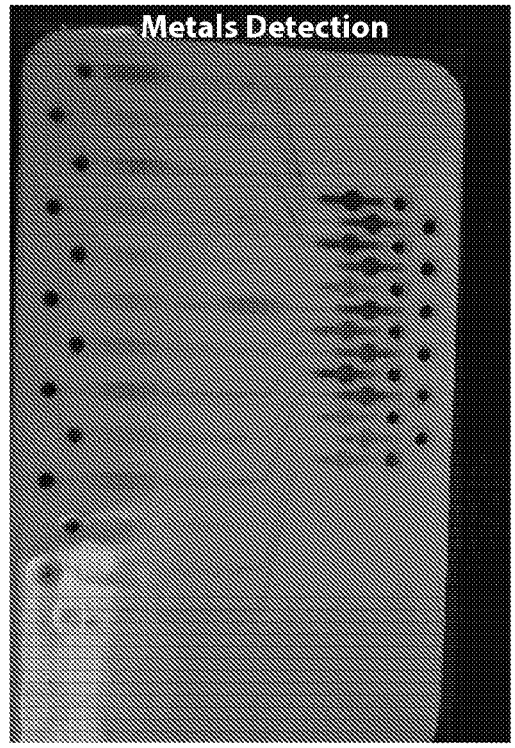
FIG. 9 shows a photograph of the colorimetric response of a device upon exposure to metals.
Figure 10:
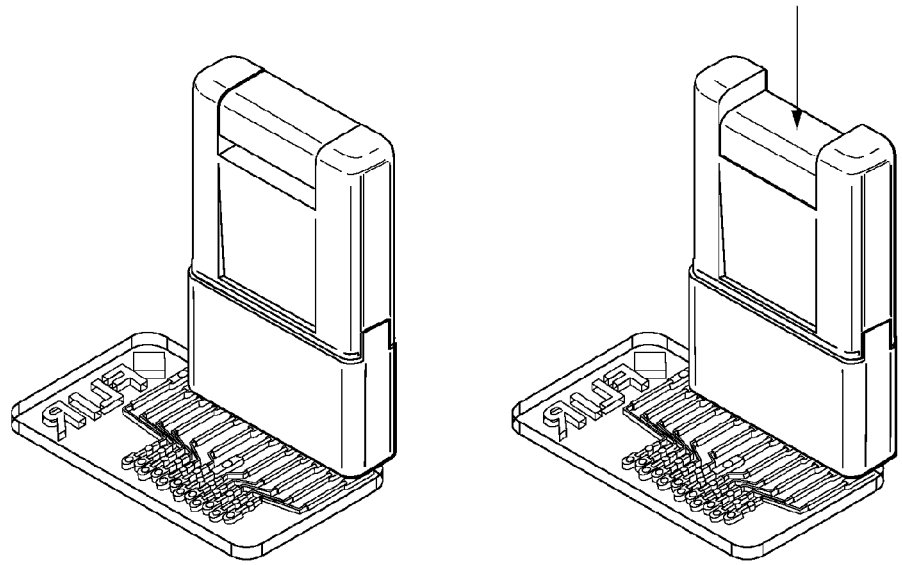
Figure 3:
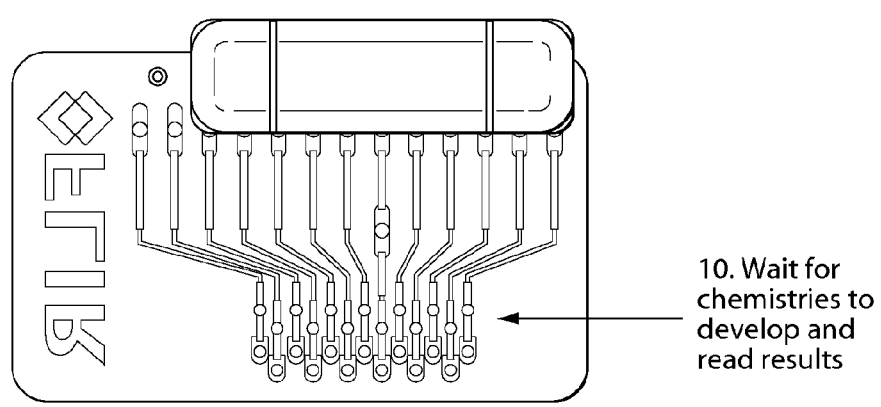

FIG. 9 shows the detection of metals. A fluid sample containing magnesium salts was injected into the prototype sample analysis device pre-loaded with metals detection reagents, at various concentrations, with the results for the highest concentrated sample shown in the top channel.

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed:
1. A method for determining an analyte, comprising:
  introducing a sample suspected of containing an analyte into a sample inlet of a sample analysis device, the sample analysis device comprising a plurality of channels constructed and arranged to receive the sample suspected of containing an analyte from the sample inlet, each channel comprising a different chemical reagent, each chemical reagent capable of generating a luminescent or colorimetric signal;
  treating the sample with a plurality of different solvents provided from a corresponding plurality of solvent chambers disposed within the sample analysis device, wherein the plurality of solvent chambers are in fluid communication with the sample inlet; and
  simultaneously introducing the treated sample into the plurality of channels such that the analyte, if present, interacts with one or more of the chemical reagents to produce a plurality of luminescent or colorimetric signals, thereby determining the analyte, wherein the plurality of channels are in fluid communication with the sample inlet, and wherein the presence and/or identity of the analyte is determined without need for a non-luminescent or non-colorimetric analysis of the sample.

2. A method as in claim 1, wherein the chemical reagents are in substantially solid form.

3. A method as in claim 1, wherein the sample analysis device comprises:
at least five channels; and
a sample collection pad with a gas permeable filter configured to receive and filter the sample at the sample inlet;
a mixing chamber located downstream from and in fluid communication with the sample inlet,
wherein the plurality of solvent chambers comprise at least three blister buttons disposed within the sample analysis device and in fluid communication with the mixing chamber to provide at least three different solvents sequentially to treat the sample at the mixing chamber before the sample is introduced into the at least five channels.

4. A method as in claim 1, wherein at least one channel comprises a reaction well containing the chemical reagent, wherein at least a portion of the sample contacts the chemical reagent.

5. A method as in claim 1, wherein at least one channel comprises a first reaction well containing a pre-treatment reagent and a second reaction well containing a chemical reagent, the second well positioned downstream from the first reaction well, wherein at least a portion of the sample first contacts the pre-treatment reagent and then subsequently contacts the chemical reagent.

6. A method as in claim 1, wherein at least one channel comprises a first reaction well containing a first chemical reagent and a second reaction well containing a second chemical reagent, the second well positioned downstream from the first reaction well, wherein at least a portion of the sample first contacts the first chemical reagent and then subsequently contacts the second chemical reagent.

7. A method as in claim 1, wherein at least one channel comprises a mixing region positioned downstream from a reaction well containing the chemical reagent, such that a mixture comprising the sample and the chemical reagent are allowed to react to produce a luminescent or colorimetric signal.

8. A method as in claim 1, wherein at least one channel comprises a detection well positioned downstream from a mixing region, wherein the luminescent or colorimetric signal is determined within the detection well.

9. A method as in claim 1, wherein the analyte is a drug, chemical warfare agent, biological warfare agent, toxic industrial chemical, or toxic industrial metal.

10. A method as in claim 1, wherein the analyte is gun powder or gunshot residue, TNT, DNT, tetryl, nitroglycerin, EGDN, PETN, RDX, HMX, nitrate, chlorate, perchlorate, permanganate, peroxide-based explosive, Al, Mg, or a precursor thereof.

11. A method as in claim 1, wherein the analyte is present in water.

12. A method as in claim 1, wherein the chemical reagent comprises a reagent capable of forming a Meisenheimer complex, a reagent capable of undergoing a Griess reaction, p-DMAC, Berthlot's reagent, aniline sulfate, [Pt(tpy)Cl]PF$_6$, a boronate-containing species, diphenylamine, aluminon, diaminobenzene, a pyrocatechol violet reagent, or a nitrophenylazoresorcinal reagent.

13. A method as in claim 1, wherein the sample analysis device is free of a non-luminescent reagent or non-colorimetric reagent.

14. A method as in claim 1, wherein the sample analysis device does not comprise a crystallizing agent.

15. A method as in claim 1, wherein the sample is collected by contacting a surface of a sample collection device with an article suspected of containing the analyte.

16. A method as in claim 15, further comprising:
contacting the surface of the sample collection device with a fluid carrier provided in the sample collection device to produce a fluid sample containing the analyte, if present.

17. A method as in claim 16, wherein the fluid carrier comprises an organic solvent.

18. A method as in claim 15, further comprising:
contacting the surface of the sample collection device with a fluid carrier provided in the sample collection device to produce a fluid sample containing the analyte, if present, wherein the fluid sample is introduced to the sample analysis device.

19. A method as in claim 15, wherein the surface is a substantially planar surface.

20. A method as in claim 15, wherein the surface is the surface of a rolling substrate.

21. A method as in claim 20, wherein the rolling substrate comprises an adhesive material.

22. A method as in claim 15, wherein the sample collection device and the sample analysis device are provided together in a kit.

23. A method for determining an analyte, comprising:
contacting a surface of a rolling substrate of a sample collection device with an article suspected of containing an analyte via a rolling or tapping motion such that a sample suspected of containing the analyte is collected on the surface of the rolling substrate;
contacting the surface of the rolling substrate with a fluid carrier to transfer at least a portion of the sample to the fluid carrier to produce a fluid sample suspected of containing the analyte;
introducing the fluid sample suspected of containing the analyte into a sample inlet of a sample analysis device comprising a plurality of channels constructed and arranged to receive the fluid sample;
treating the fluid sample with a plurality of solvents provided from a corresponding plurality of solvent chambers disposed within the sample analysis device, wherein the plurality of solvent chambers are in fluid communication with the sample inlet;
simultaneously introducing portions of the fluid sample into each of a set of the plurality of channels, each of the set of channels comprising a different chemical reagent capable of generating a luminescent and/or colorimetric signal upon interaction with a specific analyte, wherein the analyte, if present in the fluid sample, interacts with one or more of the chemical reagents to produce a plurality of luminescent and/or colorimetric signals in at least some of the set of channels, wherein the plurality of channels are in fluid communication with the sample inlet; and
determining the presence and/or identity of the analyte based on the plurality of luminescent and/or colorimetric signals.

24. A kit for determining an analyte, comprising:
a sample collection device, comprising:
a first region comprising a fluid container containing a fluid carrier;

a second region comprising a surface constructed and arranged to contact an article suspected of containing the analyte and to receive fluid from the fluid container;

a sample outlet in fluid communication with the first and second regions; and a housing containing the first region, the second region, and the sample outlet; and a sample analysis device, comprising:

at least one sample inlet constructed and arranged to receive a sample suspected of containing an analyte from the sample outlet of the sample collection device;

a plurality of solvent chambers disposed within the sample analysis device and providing a plurality of different solvents for dissolving the sample, wherein the plurality of solvent chambers are in fluid communication with the at least one sample inlet; and a channel in fluid communication with the at least one sample inlet and configured to receive the dissolved sample, the channel comprising a chemical reagent capable of generating a luminescent or colorimetric signal.

* * * * *